US007297847B1

(12) United States Patent
Ludevid et al.

(10) Patent No.: US 7,297,847 B1
(45) Date of Patent: Nov. 20, 2007

(54) AMINO ACID-ENRICHED PLANT PROTEIN RESERVES, PARTICULARLY LYSINE-ENRICHED MAIZE γ-ZEIN, AND PLANTS EXPRESSING SUCH PROTEINS

(75) Inventors: Dolorès Ludevid, Barcelone (ES); Margarita Torrent, Barcelone (ES); Inaki Alvarez, Barcelone (ES); Pascual Perez, Beaumont (FR)

(73) Assignee: Biogemma, Paris (FR)

( * ) Notice: Subject to any disclaimer, the term of this patent is extended or adjusted under 35 U.S.C. 154(b) by 0 days.

(21) Appl. No.: 09/117,246

(22) PCT Filed: Jan. 28, 1997

(86) PCT No.: PCT/FR97/00167

§ 371 (c)(1),
(2), (4) Date: Dec. 3, 1998

(87) PCT Pub. No.: WO97/28247

PCT Pub. Date: Aug. 7, 1997

(30) Foreign Application Priority Data

Jan. 29, 1996 (FR) .................................. 96 01004

(51) Int. Cl.
| C12N 15/29 | (2006.01) |
| C12N 15/63 | (2006.01) |
| C12N 15/82 | (2006.01) |
| A01H 5/00 | (2006.01) |
| A01H 5/10 | (2006.01) |
| A01H 5/12 | (2006.01) |

(52) U.S. Cl. .................... 800/320.1; 800/287; 800/298; 435/419; 435/320.1; 536/23.1; 536/23.4; 536/23.6

(58) Field of Classification Search ................ 800/278, 800/298, 320.1; 536/23.1, 23.6; 435/419, 435/424, 320.1
See application file for complete search history.

(56) References Cited

FOREIGN PATENT DOCUMENTS

| EP | 0 208 418 A2 | | 1/1989 |
| EP | 0 318 341 A1 | | 5/1989 |
| EP | 0 131 623 B1 | | 3/1991 |
| WO | WO 91/13991 | * | 9/1991 |
| WO | WO 93/12230 | | 6/1993 |
| WO | WO 93/15221 | * | 8/1993 |
| WO | WO 95/06128 | | 3/1995 |

OTHER PUBLICATIONS

GenBank Accession No. M19784, 1988.*
GenBank Accession S42552.*
GenBank Accession M19784.*
Alvarez I. et al. Planta, 1998, vol. 205; pp. 420-427.*
Gaisser, S. Molecular Microbiology 1991, vol. 5, No. 11; pp. 2777-2787; submitted as GenBank Accession No. S80675.*
Ohanti T. et al. Plant Molecular Biology, 1991, vol. 16; pp. 117-128; see Abstract.*
Torrent M et al. 1997, Plant Molecular Biology, vol. 34, pp. 139-149; see Abstract.*
Coleman C. et al. The Plant Cell, vol. 8; pp. 2335-2345; see p. 2341 col. 2 last paragraph to p. 2342 col. 1 line 8.*
Boronat et al., "Isolation and Sequence of a 28kD Glutelin-2 Gene from Maize. Common Elements in the 5' Flanking Regions among Zein and Glutelin, " *Plant Sci.*, 47:95-102, 1986.
Falco et al., "Transgenic Canola and Soybean Seeds with Increased Lysine," *Bio Technology*, 13:577-582, 1995.
Forney et al., EMBL Sequence Database, Rel. 18, Accession No. M19784, (1989).
Geetha et al., "Opaque-2 Modifiers Increase γ-Zein Synthesis and Alter its Spatial Distribution in Maize Endosperm," *Plant Cell*, 3:1207-1219, 1991.
Geli et al., "Two Structural Domains Mediate Two Sequential Events in γ-Zein Targeting: Protein Endoplasmic Reticulum retention and Protein Body Formation," *Plant Cell*, 6:1911-1922, 1994.
Hagen et al., "Complex Organization of Zein Genes in Maize," *Gene*, 12: 239-249, 1980.
Hillier et al., EMBL Sequence Database Accession No. R40179, Release 43, (1995).
GCG-Geneseq Database Accession No. R28869 (1993) and WO92 19248 (1992).
Lending et al., "Changes in the Zein Composition of Protein Bodies during Maize Endosperm Development," *Plant Cell*, 1:10111-1033, 1984.
Lopes et al., "Identification of Two Opaque2 Modifier Loci in Quality Protein Maize," *Mol. Gen. Genet.*, 247:603-613, 1995.
Lopes et al., "Genetic Analysis of Opaque2 Modifier Gene Activity in Maize Endosperm," *Theor. Appl. Genet.*, 19:274-281, 1995.
Ludevid et al., "Immunological Relations Between Glutelin-2 and Low Molecular Weight Zein-2 Proteins from Maize (*Zea Mays* L) Endosperm,"*Plant Sci.*, 41:41-18. 1985.
Ludevid et al., "Subcellar Localization of Glutelin-2 in Maize (*Zea Mays* L.) Endosperm," *Plant Mol. Biol.*, 3:227-234, 1984.
Mertz et al., "Mutant Gene That Changes Protein Composition and Increases Lysine Content of Maize Endosperm." *Science*, 145: 279-280. 1964.
Nelson et al., "Second Mutant Gene Affecting the Amino Acid Pattern of Maize Endosperm Proteins," *Science*, 150:1469-1470, 1965.
Ohtani et al., "Normal and Lysine-containing Zeins are Unstable in Transgenic Tobacco Seeds," *Plant Mol. Biol.*, 16:117, 1991.
Perl et al., "Regulation of Lysine Synthesis in Transgenic Potato Plants Expressing a Bacterial Dihydrodipicolinate Synthase in their Chloroplasts," *Plant Mol. Biol.* 19: 815-823. 1992.

(Continued)

*Primary Examiner*—Russell P. Kallis
(74) *Attorney, Agent, or Firm*—Clark & Elbing, LLP

(57) ABSTRACT

An oligonucleotide including at least one concatenation coding for a polypeptide of formula $(P—K)_n$, wherein n is an integer of at least 2, P is a proline amino acid residue, K is a lysine amino acid residue, and the sign "—" is a bond, particularly a peptide bond, between the two amino acid residues. The n (P—K) units are also bound together by such bonds, e.g. peptide bonds.

44 Claims, 17 Drawing Sheets

OTHER PUBLICATIONS

Figure 1:
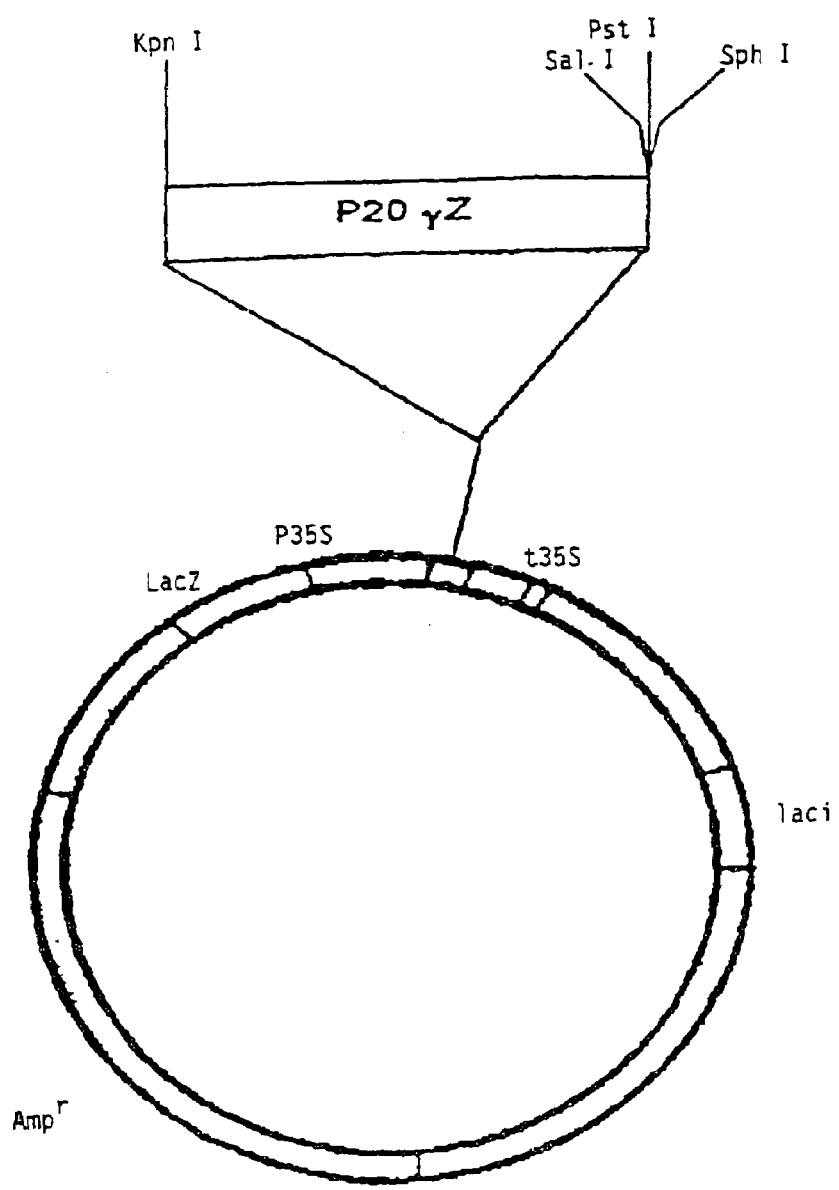

Prat et al., "Nucleic Acid (cDNA) and Amino Acid Sequences of the Maize Endosperm Protein Glutelin-2," *Nud. Acids Res*. 13: 1494-1504. 1985.

Qi et al., "Reconstitution of Neuronal Cdc2-like Kinase from Bacteria-expressed Cdk5 and an Active Fragment of the Brain-specific Activator." The Journal of Biological Chemistry. 270(18):1084-10854 (1995).

Reina et al., "Sequence Analysis of a Genomic Clone Encoding a Zc2 Protein from *Zea mays* W64 A, " *Nucl. Acids Res*, 18:6426, 1990.

Schmidt et al., "Maize Regulatory Gene Opaque-2 Encodes a Protein with a "Leucine-zipper" Motif that Binds to Zein DNA." *Proc. Natl. Acad. Sci USA*. 87:46-50. 1990.

Shaul et al., "Increased Lysine Synthesis in Tobacco Plants that Express High Levels of Bacterial Dihydrodipicolinate Synthase in their Chloroplasts," *Plant J* . 2:203-209, 1992.

Shaul et al., "Concerted Regulation of Lysine and Threonine Synthesis in Tobacco Plants Expressing Bacterial Feedback-insensitive Aspartate Kinase and Dihydrodipicolinate Synthase," *Plant Mol. Biol.*, 23:759-768, 1993.

Torrent et al. "Lysine-rich modified γ-zeins accumulate in protein bodies of transiently transformed maize endosperms," Plant Molecular Biology, 34:139-149 (1997).

Torrent et al., "Storage-protein Hydrolysis and Protein-body Breakdown in Germinated *Zea mays* L. Seeds," *Planta*, 180:90-95, 1989.

Torrent et al., "Role of Structural Domains for Maize γ-zein Retention in Xenopus Oocytes," *Planta*, 192:512-518, 1994.

Wallace et al., "Aggregation of Lysine-Containing Zeins into Protein Bodies in Xenopus Oocytes,"*Science*, 240:662-664. 1988.

\* cited by examiner

γ-Zéine

```
              10        20        30        40        50        60
               |         |         |         |         |         |
        ATGAGGGTGTTGCTCGTTGCCCTCGCTCTCCTGGCTCTCGCTGCGAGCGCCACCTCCACG
         M  R  V  L  L  V  A  L  A  L  L  A  L  A  A  S  A  T  S  T 70        80        90       100       110       120
               |         |         |         |         |         |
        CATACAAGCGGCGGCTGCGGCTGCCAGCCACCGCCGCCGGTTCATCTACCGCCGCCGGTG
         H  T  S  G  G  C  G  C  Q  P  P  P  P  V  H  L  P  P  P  V 130       140       150       160       170       180
               |         |         |         |         |         |
        CATCTGCCACCTCCGGTTCACCTGCCACCTCCGGTGCATCTCCCACCGCCGGTCCACCTG
         H  L  P  P  P  V  H  L  P  P  P  V  H  L  P  P  P  V  H  L 190       200       210       220       230       240
               |         |         |         |         |         |
        CCGCCGCCGGTCCACCTGCCACCGCCGGTCCATGTGCCGCCGCCGGTTCATCTGCCGCCG
         P  P  P  V  H  L  P  P  P  V  H  V  P  P  P  V  H  L  P  P 250       260       270       280       290       300
               |         |         |         |         |         |
        CCACCATGCCACTACCCTACTCAACCGCCCCGGCCCTCAGCCTCATCCCCAGCCACACCCA
         P  P  C  H  Y  P  T  Q  P  P  R  P  Q  P  H  P  Q  P  H  P 310       320       330       340       350       360
               |         |         |         |         |         |
        TGCCCGTGCCAACAGCCGCATCCAAGCCCGTGCCAGCTGCAGGGAACCTGCGGCGTTGGC
         C  P  C  Q  Q  P  H  P  S  P  C  Q  L  Q  G  T  C  G  V  G 370       380       390       400       410       420
               |         |         |         |         |         |
        AGCACCCCGATCCTGGGCCAGTGCGTCGAGTTTCTGAGGCATCAGTGCAGCCCGACGGCG
         S  T  P  I  L  G  Q  C  V  E  F  L  R  H  Q  C  S  P  T  A 430       440       450       460       470       480
               |         |         |         |         |         |
        ACGCCCTACTGCTCGCCTCAGTGCCAGTCGTTGCGGCAGCAGTGTTGCCAGCAGCTCAGG
         T  P  Y  C  S  P  Q  C  Q  S  L  R  Q  Q  C  C  Q  Q  L  R 490       500       510       520       530       540
               |         |         |         |         |         |
        CAGGTGGAGCCGCAGCACCGGTACCAGGCGATCTTCGGCTTGGTCCTCCAGTCCATCCTG
         Q  V  E  P  Q  H  R  Y  Q  A  I  F  G  L  V  L  Q  S  I  L 550       560       570       580       590       600
               |         |         |         |         |         |
        CAGCAGCAGCCGCAAAGCGGCCAGGTCGCGGGGCTGTTGGCGGCGCAGATAGCGCAGCAA
         Q  Q  Q  P  Q  S  G  Q  V  A  G  L  L  A  A  Q  I  A  Q  Q
```

FIGURE 9

```
          610       620       630       640       650       660
           |         |         |         |         |         |
CTGACGGCGATGTGCGGCCTGCAGCAGCCGACTCCATGCCCCTACGCTGCTGCCGGCGGT
 L  T  A  M  C  G  L  Q  Q  P  T  P  C  P  Y  A  A  A  G  G

670
           |
GTCCCCCACTGA
 V  P  H  -
```

FIGURE 9 (CONTINUED)

H45 γ Z

```
          10         20         30         40         50         60
           |          |          |          |          |          |
ATGAGGGTGTTGCTCGTTGCCCTCGCTCTCCTGGCTCTCGCTGCGAGCGCCACCTCCACG
 M  R  V  L  L  V  A  L  A  L  L  A  L  A  A  S  A  T  S  T 70         80         90        100        110        120
           |          |          |          |          |          |
CATACAAGCGGCGGCTGCGGCTGCCAGCCACCGCCGCCGGTTCATCTACCGCCGCCGGTG
 H  T  S  G  G  C  G  C  Q  P  P  P  P  V  H  L  P  P  P  V 130        140        150        160        170        180
           |          |          |          |          |          |
CATCTGCCACCTCCGGTTCACCTGCCACCTCCGGTGCATCTCCCACCGCCGGTCCACCTG
 H  L  P  P  P  V  H  L  P  P  P  V  H  L  P  P  P  V  H  L 190        200        210        220        230        240
           |          |          |          |          |          |
CCGCCGCCGGTCCACCTGCCACCGCCGGTCCATGTGCCGCCGCCGGTTCATCTGCCGCCG
 P  P  P  V  H  L  P  P  P  V  H  V  P  P  P  V  H  L  P  P 250        260        270        280        290        300
           |          |          |          |          |          |
CCACCATGCCACTACCCTACTCAACCGCCCCGGATCGAATTCAAACCAAAGCCAAAGCCG
 P  P  C  H  Y  P  T  Q  P  P  R  I  E  F  K  P  K  P 310        320        330        340        350        360
           |          |          |          |          |          |
AAGCCAAAAGAATTCAAACCAAAGCCAAAGCCGAAGCCAAAAGAATTCCTGCAGCCCCTG
 K  P  K  E  F  K  P  K  P  K  P  K  P  K  E  F  L  Q  P  L 370        380        390        400        410        420
           |          |          |          |          |          |
CAGGGAACCTGCGGCGTTGGCAGCACCCCGATCCTGGGCCAGTGCGTCGAGTTTCTGAGG
 Q  G  T  C  G  V  G  S  T  P  I  L  G  Q  C  V  E  F  L  R 430        440        450        460        470        480
           |          |          |          |          |          |
CATCAGTGCAGCCCGACGGCGACGCCCTACTGCTCGCCTCAGTGCCAGTCGTTGCGGCAG
 H  Q  C  S  P  T  A  T  P  Y  C  S  P  Q  C  Q  S  L  R  Q 490        500        510        520        530        540
           |          |          |          |          |          |
CAGTGTTGCCAGCAGCTCAGGCAGGTGGAGCCGCAGCACCGGTACCAGGCGATCTTCGGC
 Q  C  C  Q  Q  L  R  Q  V  E  P  Q  H  R  Y  Q  A  I  F  G 550        560        570        580        590        600
           |          |          |          |          |          |
TTGGTCCTCCAGTCCATCCTGCAGCAGCAGCCGCAAAGCGGCCAGGTCGCGGGGCTGTTG
 L  V  L  Q  S  I  L  Q  Q  Q  P  Q  S  G  Q  V  A  G  L  L 610        620        630        640        650        660
           |          |          |          |          |          |
GCGGCGCAGATAGCGCAGCAACTGACGGCGATGTGCGGCCTGCAGCAGCCGACTCCATGC
 A  A  Q  I  A  Q  Q  L  T  A  M  C  G  L  Q  Q  P  T  P  C
```

FIGURE 10

```
              670           680           690
               |             |             |
         CCCTACGCTGCTGCCGGCGGTGTCCCCCACTGA
          P   Y   A   A   A   G   G   V   P   H   -
```

FIGURE 10 (CONTINUED)

P20 γZ

```
          10        20        30        40        50        60
          |         |         |         |         |         |
ATGAGGGTGTTGCTCGTTGCCCTCGCTCTCCTGGCTCTCGCTGCGAGCGCCACCTCCACG
 M  R  V  L  L  V  A  L  A  L  L  A  L  A  A  S  A  T  S  T 70        80        90       100       110       120
          |         |         |         |         |         |
CATACAAGCGGCGGCTGCGGCTGCCAGCCACCGCCGCCGGTTCATCTACCGCCGCCGGTG
 H  T  S  G  G  C  G  C  Q  P  P  P  V  H  L  P  P  P  V 130       140       150       160       170       180
          |         |         |         |         |         |
CATCTGCCACCTCCGGTTCACCTGCCACCTCCGGTGCATCTCCCACCGCCGGTCCACCTG
 H  L  P  P  P  V  H  L  P  P  P  V  H  L  P  P  P  V  H  L 190       200       210       220       230       240
          |         |         |         |         |         |
CCGCCGCCGGTCCACCTGCCACCGCCGGTCCATGTGCCGCCGCCGGTTCATCTGCCGCCG
 P  P  P  V  H  L  P  P  P  V  H  V  P  P  P  V  H  L  P  P 250       260       270       280       290       300
          |         |         |         |         |         |
CCACCATGCCACTACCCTACTCAACCGCCCCGGCCTCAGCCTCATCCCCAGCCACACCCA
 P  P  C  H  Y  P  T  Q  P  P  R  P  Q  P  H  P  Q  P  H  P 310       320       330       340       350       360
          |         |         |         |         |         |
TGCCCGTGCCAACAGCCGCATCCAAGCCCGTGCCAGATCGAATTCAAACCAAAGCCAAAG
 C  P  C  Q  Q  P  H  P  S  P  C  Q  I  E  F  K  P  K  P  K 370       380       390       400       410       420
          |         |         |         |         |         |
CCGAAGCCAAAAGAATTCCTGCAGCCCCTGCAGGGAACCTGCGGCGTTGGCAGCACCCCG
 P  K  P  K  E  F  L  Q  P  L  Q  G  T  C  G  V  G  S  T  P 430       440       450       460       470       480
          |         |         |         |         |         |
ATCCTGGGCCAGTGCGTCGAGTTTCTGAGGCATCAGTGCAGCCCGACGGCGACGCCCTAC
 I  L  G  Q  C  V  E  F  L  R  H  Q  C  S  P  T  A  T  P  Y 490       500       510       520       530       540
          |         |         |         |         |         |
TGCTCGCCTCAGTGCCAGTCGTTGCGGCAGCAGTGTTGCCAGCAGCTCAGGCAGGTGGAG
 C  S  P  Q  C  Q  S  L  R  Q  Q  C  C  Q  Q  L  R  Q  V  E 550       560       570       580       590       600
          |         |         |         |         |         |
CCGCAGCACCGGTACCAGGCGATCTTCGGCTTGGTCCTCCAGTCCATCCTGCAGCAGCAG
 P  Q  H  R  Y  Q  A  I  F  G  L  V  L  Q  S  I  L  Q  Q  Q 610       620       630       640       650       660
          |         |         |         |         |         |
CCGCAAAGCGGCCAGGTCGCGGGGCTGTTGGCGGCGCAGATAGCGCAGCAACTGACGGCG
 P  Q  S  G  Q  V  A  G  L  L  A  A  Q  I  A  Q  Q  L  T  A
```

FIGURE 11

```
          670       680       690       700       710       720
           |         |         |         |         |         |
ATGTGCGGCCTGCAGCAGCCGACTCCATGCCCCTACGCTGCTGCCGGCGGTGTCCCCCAC
 M  C  G  L  Q  Q  P  T  P  C  P  Y  A  A  A  G  G  V  P  H

TGA
 -
```

FIGURE 11 (CONTINUED)

AMINO ACID-ENRICHED PLANT PROTEIN RESERVES, PARTICULARLY LYSINE-ENRICHED MAIZE γ-ZEIN, AND PLANTS EXPRESSING SUCH PROTEINS

This Application is the U.S. national phase of international application PCT/FR97/00167 filed 28 Jan. 1997, which designated the U.S. and claims benefit of FR 96/01004 filed Jan. 29, 1996.

The present application relates to novel means enabling plants expressing protein reserves which are enriched in amino acids and which are deficient in normal protein reserves to be prepared, in particular to lysine-enriched protein reserves. The invention also provides the thus modified protein reserves, and plants expressing these modified protein reserves.

Many plants, some after transformation using physico-chemical steps, are of major economic importance for human or animal foodstuffs, and the problem of improving their nutritional quality has already given rise to different types of research. In particular, to overcome the insufficiency of certain amino acids in plant protein reserves, selected varieties have been developed which have superior nutritional qualities, or different modifications have been proposed which use genetic engineering techniques to encourage or increase production in such plants of certain deficient amino acids which are nevertheless important for the nutritional qualities of the plant. Examples of deficient amino acids are lysine and methionine.

Within the context of the present application, the inventors have proposed an original solution to the problem of improving plants, in particular improving their nutritional qualities, in the first instance using a plant of considerable economic importance, namely maize. More precisely, they have concentrated on the protein reserves in maize seed endosperm, which comprise zeins, in particular γ-zein.

As maize seeds develop, the cells of the endosperm synthesise large quantities of protein reserves, in particular α-, β- and γ-zeins. Such zeins are accumulated in protein bodies derived from the endoplasmic reticulum (ER).

In general, zeins represent a complex protein group divided into a number of groups, α-, β-, γ- and δ-zeins (Larkins et al., 1989) encoded by a multigenic family (Hagen and Rubenstein, 1980, Gene 13, 239-249). While their structure is variable, such proteins have common features: the presence of tandem repeats in their primary structure which are rich in proline type amino acid residues, the presence of numerous hydrophobic residues which result in the insolubility of such proteins in aqueous media, and the absence of lysine residues, essential amino acids for man and for monogastric animals. The absence of lysine in all of the major proteins (detected in large quantities in the endosperm) naturally produced in the zein group leads to an unbalanced amino acid composition in maize seeds.

Of such proteins, maize γ-zein is a protein with a molecular weight of 28 kDa, the coding sequence for which has been described in the cDNA form by Prat et al. (Nucleic Acids Research, vol. 13, no 5, 1985, p 1494-1504). The complete sequence of the gene coding for the γ-zein, including the upstream and downstream non coding sequences containing the expression regulation elements, has been described by M. Reina et al. (Nucleic Acids Research, vol. 18, no 21, 1990, p 6426).

Up until now, different approaches have been envisaged for increasing the amount of lysine in proteins of the zein group. In this respect, genetic and molecular approaches have been carried out. As an example, mutants for obtaining lysine-rich maize such as opaque-2 mutant (o2) and flour-2 mutant (fl-2) (Mertz et al., 1964, Science 145, 279-280, Nelson et al., 1965, Science 150, 1469-1470) have been proposed and attempts have been made to remedy the deleterious effects of the absence of certain classes of zeins, in particular α-zeins, on the phenotype characteristics by selecting maize containing o2 modifying genes (Paez et al., 1969, Plant Sci. 9, 251-252, Geetha et al., 1991, Plant Cell 3, 1207-1219).

Another approach has consisted in taking indirect action on the production of free lysine, in particular in dicotyledonous plants. That technique involved deregulating key enzymes (DHTPS and AK) involved in the lysine via aspartate biosynthesis cycle. A cross sensitive to the levels of free lysine was obtained in the leaves, but not in the seeds, in tobacco plant transformation experiments with $E.$ $Coli$ bacteria containing dapA genes and $E.$ $Coli$ bacteria containing the lysC gene (Shaul and Galili, 1992, Plant J. 2, 203-209 and 1993, Plant Mol. Biol. 23, 759-768; Perl. A., Schaul O., Galili. G., 1992, Plant Molecular Biology 19, p 815-823). Recently, the same genes, dapA from $Corynebacterium$ and lysC from $E.$ $Coli$, were used and expressed under the control of a specific promoter of seeds in soya plants. Expression of these two enzymes in soya led to a five times increase in the amount of lysine in the seeds (Falco et al., 1995, BIO-Technology 13, 577-582).

Other authors (Wallace et al., 1988, Science 240, 662-664) attempted to increase the lysine in α-zein (19 kDa) in maize seeds by point incorporation of lysine residues at different positions in the α-zein molecule. Expression of these constructs in $Xenopus$ oocytes led to proper assembly of lysine-rich zeins in analogous vesicles of protein bodies. However, the normal α-zein and the lysine-enriched modified form were degraded when they were expressed in tobacco seeds (Othani et al., 1991, Plant Mol. Biol., 16:117).

Thus there is currently no knowledge regarding the means which could enable expression of a lysine-enriched zein in cells producing it naturally in maize, i.e., in the endosperm cells. A fortiori, expression of lysine-enriched zeins in other plant cells has not been mastered.

One aim of the invention is thus to provide means for obtaining a lysine-enriched zein, in particular a lysine-enriched maize γ-zein, this protein being expressed particularly in maize seed cells and in particular in endosperm cells, said modified protein further being expressed such that its properties as regards localisation and accumulation in the endoplasmic reticulum and derivative protein bodies are preserved.

The expression "lysine-enriched" used in the present application means that the protein includes an increased number of lysine residues with respect to the natural protein from which it is derived, for example as a result of modifying the nucleotide sequence expressing it.

The invention also provides means for obtaining expression of proteins, preferably lysine-enriched γ-zeins, in plant cells of different tissues, for example leaf tissue or root tissue, and if necessary in the cells of plants which do not naturally express the protein, in particular the γ-zein the production of which is desired.

In addition, in one particular implementation of the invention, other protein reserves can be enriched in lysine under analogous conditions.

In a first aspect, the inventors propose to introduce into the gene coding for the γ-zein or for other protein reserves of maize or other plants, or into the coding sequence of this gene, sequences coding for lysine-enriched polypeptides, in order to produce lysine-enriched γ-zeins or other proteins and thus to produce lysine-enriched seeds. Different sites in the coding sequence of the γ-zein gene have been identified as allowable sites (also known as neutral sites) to prepare the modified nucleotide sequences.

The present application thus proposes means for transforming the gene coding for the maize γ-zein or for transforming any nucleotide sequence coding for the γ-zein and derived from that gene, so as to obtain, by expression of the modified gene or, more generally, of the modified nucleotide sequence, a lysine-enriched protein; these means in particular include synthetic oligonucleotides coding for an amino acid sequence comprising lysine residues.

The invention also provides recombinant nucleotide sequences or chimeral sequences which can code for a lysine-enriched γ-zein.

Still further, the invention provides host cells transformed by such sequences, in particular plant cells, for example cells enabling plant regeneration, also plants or plant portions (tissues, organs . . . ) containing such cells and producing modified protein reserves in a stable manner, in particular lysine-enriched γ-zeins.

The invention also encompasses said modified proteins, for example lysine-enriched proteins, and antibodies directed against these proteins.

An appropriate oligonucleotide for carrying out the invention for use in preparing recombinant nucleotide sequences is characterized in that it comprises at least one concatenation coding for a polypeptide with formula $(P—K)_n$, where:
  n is a whole number of 2 or more;
  P represents a proline amino acid residue;
  K represents a lysine amino acid residue;
  the symbol "—" represents a bond between the two amino acid residues, in particular a peptide type bond, the n (P—K) units also being bonded together by such bonds, for example peptide type bonds.

In a first embodiment, an oligonucleotide of the invention is thus characterized in that it comprises a sequence coding for a series of repeated moieties comprising two amino acids.

The oligonucleotide codons may be identical for all of the proline and/or for all of the lysine residues. They may also be different for the same amino acid residue, the variation taking the degeneracy of the genetic code into account.

This oligonucleotide is preferably formed by a sequence coding for more than 2 (P—K) units. Preferably, n is 30 or less (SEQ ID NO:22), in particular below 20 and advantageously, n equals 4 (SEQ ID NO:13), 5 (SEQ ID NO:14), 6 (SEQ ID NO:15), 7 (SEQ ID NO:16), 8 (SEQ ID NO:17), 9 (SEQ ID NO:18), or 10 (SEQ ID NO:19), or 15 (SEQ ID NO:20).

The "oligonucleotides" of the invention can be chemically synthesised using any available technique.

The term "polypeptide" referring to the concatenation $(P—K)_n$ as used in the present invention means a sequence of amino acids containing more than 2 amino acid residues and which may comprise up to 60 amino acid residues.

In a first variation of the invention, the oligonucleotide comprises several concatenations coding for a polypeptide with formula $(P—K)_n$, identical or different, associated in tandem.

These oligonucleotides are either repeats of a single concatenation, or associations of different concatenations. The number of associated concatenations can vary, for example in the range 2 to 10 concatenations.

In a further variation of the invention, the oligonucleotide defined above is characterized in that it comprises at least one concatenation coding for a polypeptide with formula $(P—K)_n$, in which the sequence of n (P—K) units is interrupted by one or more amino acid residues other than P or K residues.

The supplemental amino acids incorporated into the sequence formed by the (P—K) units are preferably selected so as not to modify the organisation of the polypeptide coded by the oligonucleotide, or at the very least not to cause interaction with the amino acids of a protein into which said polypeptide would be incorporated, under conditions which would affect the structure and/or function and/or localisation of this protein.

This can in particular be the case when the number of (P—K) units is high or when several concatenations formed from sequences coding for $(P—K)_n$ moieties are associated in tandem and when the preparation of the corresponding oligonucleotide requires that several nucleotide sequences be synthesised which are then associated by means of linkers, for example.

In a further embodiment of the invention, the oligonucleotide is such that the concatenation coding for the polypeptide comprising the n (P—K) units is completed at its 5' end and/or at its 3' end by one or more codons coding, for example, for at least one lysine residue at the N-terminal extremity of the formed polypeptide.

As an example, a preferred oligonucleotide of the invention is characterized in that it codes for a polypeptide with formula (P—K), formula $K—(P—K)_4$ (SEQ ID NO:21), or with formula $2K(P—K)_4$ (SEQ ID NO:23).

In a particular embodiment, the composition of this oligonucleotide corresponds to one of the sequences described in the following pages and identified by designations SEQ ID No: 1 and SEQ ID No:2.

The oligonucleotides described above constitute the basic resource for producing recombinant nucleotide sequences capable of expressing lysine-enriched plant protein reserves or polypeptide reserves.

The invention thus provides a recombinant nucleotide sequence comprising a concatenation of nucleotides coding for a plant protein reserve, characterized in that it further comprises an oligonucleotide of the invention, inserted at one site of the nucleotide concatenation selected such that:
  expression of the nucleotide sequence in a particular plant cell enables a modified protein reserve to be produced which is localised in that cell in a manner identical to or similar to the normal protein reserve which would be expressed in the same cell under the same conditions by the corresponding normal coding nucleotide concatenation; and/or
  the modified protein reserve coded by the nucleotide sequence is immunologically recognised by antibodies produced against the corresponding normal protein reserve.

In particular, the antibodies cited above are constituted by a polyclonal serum or are obtained against epitopes of the normal protein reserve which are conserved in the modified protein reserve.

The plant cells referred to above include any plant cell, regardless of its tissue origin or its nature. Reserve organ cells are of particular interest within the context of the invention, but also the cells of leaves, stems, tubers . . .

The expression "protein reserve" of a plant as used in the present application means a protein synthesised during seed maturation and which is used during the germination phase as the principal food reserve.

In general, it concerns a polypeptide which can be synthesised in reserve tissue regardless of its location in the plant; in particular the protein reserves used in the present invention are those produced in the grain or seed of plants in the cereal, crucifer or legume group, and are, for example, prolamins or zeins.

The choice of the site(s) for inserting the oligonucleotide in the concatenation coding for the plant protein reserve is determined by satisfying the conditions described above. Depending on the case, insertion may take place in a repeat (in terms of amino acid sequence) of the protein or at the C- or N-terminal extremity.

The condition given above in which expression of the recombinant nucleotide sequence of the invention in a plant cell enables a modified protein reserve to be obtained, localised identically or similarly to the normal protein reserve which would be expressed under the same conditions in the same plant cell, comprising, for example for synthesised γ-zeins, the possibility of being accumulated in the endoplasmic reticulum of plant cells expressing it, in particular in the protein bodies formed from the endoplasmic reticulum, when the protein is expressed in endosperm cells.

In order to obtain this result by means of the recombinant nucleotide sequences of the invention, expression systems adapted to the cell host in which the selected nucleotide sequence is expressed, and in particular the regulation elements, for example, promoters, are selected for their functional character in the tissue containing the transformed cells. Tests for making this selection can be carried out using the different constructs described in the examples.

To verify that the immunological properties of the modified protein reserve expressed by the nucleotide sequence of the invention have not been modified consequently, antiserums such as αG2 antiserum, described more precisely in the experimental section below, have been used, for example.

In a first embodiment of the invention, the recombinant nucleotide sequence is characterized in that it is obtained from a nucleotide coding concatenation which leads to expression of a protein reserve which is naturally depleted in lysine.

In general, this recombinant nucleotide sequence codes for a modified protein reserve derived from a protein reserve which is naturally produced by a plant for use in animal or human foodstuffs.

Thus protein reserves in which the lysine content has been modified within the context of the present invention are advantageously plant protein reserves from the cereal, legume or crucifer group. Particularly important protein reserves are those in maize, in particular zeins, and more particularly maize γ-zein, for which the lysine content is intended to be increased.

One particular recombinant nucleotide sequence of the invention is characterized in that the coding concatenation of nucleotides coding for the maize γ-zein, which it contains has the sequence as defined in SEQ ID NO:6.

Other recombinant nucleotide sequences of the invention are characterized in that the coding concatenation of nucleotides they comprise codes for a protein reserve of a plant selected from the following: soya, sunflower, tobacco, wheat, oats, alfalfa, rice, oilseed rape, sorghum, and *Arabidopsis*.

In a preferred embodiment of the invention, in the recombinant nucleotide sequence comprising a concatenation coding for maize γ-zein, the oligonucleotide of the invention is inserted in place of the concatenation coding for the Pro-X domain naturally present in the maize γ-zein amino acid sequence or following this concatenation. The Pro-X domain of the maize γ-zein amino acid sequence is constituted by the amino acids located between positions 70 and 91 of the amino acid sequence as defined in SEQ ID NO:7, corresponding to nucleotides 265 to 330 of the sequence as defined in SEQ ID NO:6.

Preferably, in the nucleotide sequence of the invention, the oligonucleotide in place of or following the Pro-X domain is present between nucleotides 276 and 357 of the sequence as defined in SEQ ID NO:6.

In a further embodiment of the invention, in the recombinant nucleotide sequence comprising a concatenation coding for maize γ-zein, the oligonucleotide of the invention is inserted following the Pro-X domain conserved in the maize γ-zein sequence.

In a further variation, in the recombinant nucleotide sequence comprising a concatenation coding for maize γ-zein, the oligonucleotide of the invention is inserted into the Pro-X domain maintained in the γ-zein sequence.

The above insertions can be carried out using available techniques, for example recombination of sequences which have undergone one or more enzymatic digestion steps.

In a particular embodiment of the invention, a selected protein reserve enriched in a particular amino acid is expressed in heterologous plant cells. In other words, a protein reserve which is naturally present in a given plant is expressed in an amino acid-enriched form in another plant or in a cell other than that in which it is naturally produced.

In addition to the concatenation coding for a plant protein reserve and the oligonucleotide of the invention, the recombinant nucleotide sequences of the invention can also comprise an expression promoter, for example a promoter selected for its specific expression character in certain parts or tissues of the plants, or in contrast a promoter selected for its constitutive character. As an example, when they are specific, the promoters can be specific for seeds and/or organs or particular plant tissues. They can alternatively, or also, be specific for one growth phase, for example a particular stage of germination.

In contrast, the use of constitutive promoters means expression of the protein reserve is constant and general, causing competition between expression of the native protein reserve, when it is present, and the modified protein reserve.

Figure 7:
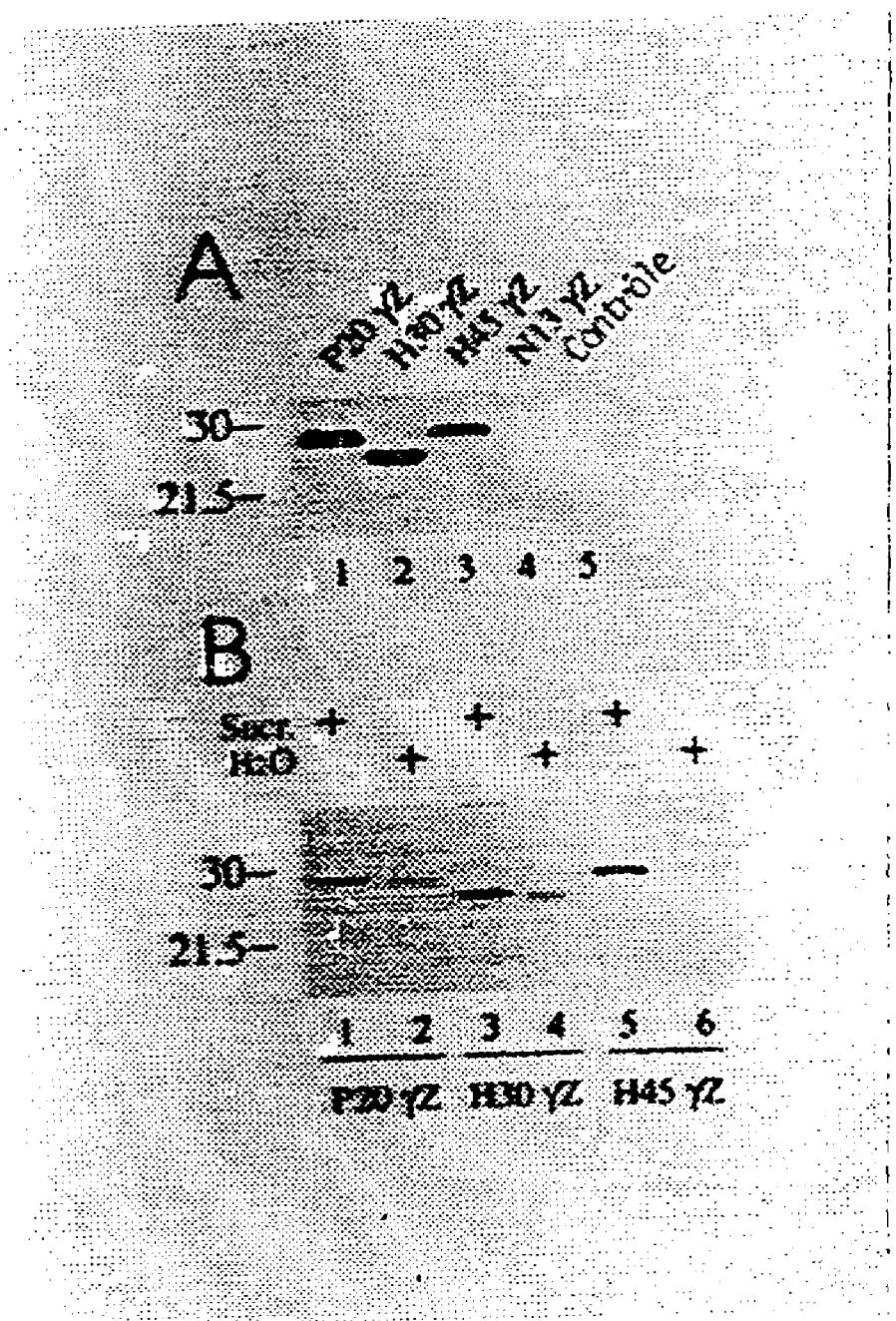

As an example, advantageous promoters for carrying out the invention are the maize γ-zein promoter contained in the 1.7 kb sequence found upstream of the coding sequence shown in FIG. 7, the cauliflower mosaic virus promoter, namely the promoter CaMV35S (European patent EP-B-0 131 623), the constitutive promoter for the actin 1 rice gene (PCT application PCT/US 9100073) or the specific "high molecular weight gluthenine" seed promoter for wheat (Colot V. et al., 1987, EMBO Journal, vol. 6, p 3559-3564).

If necessary, these promoters are completed by other regulation sequences, in particular expression activators.

Examples of other promoters which can be used in carrying out the invention are the promoter for the gene coding for the 2S protein reserve in *Arabidopsis thaliana*, or the lectin or β-phaseoline promoters for beans.

Supplemental introduction of expression activators into the regulation sequences of the nucleotide sequences of the invention can also increase the level of primary transcription of the nucleotide sequence and, if appropriate, increase the quantity of modified protein reserves produced. The activators are, for example, introns of monocotyledons such as intron 1 of the rice actin gene.

The invention also provides a cloning and/or expression vector, characterized in that it comprises, at a site which is not essential for replication, a nucleotide sequence satisfying one of the definitions given above. Examples of vectors of particular interest within the context of the present invention are the plasmids pP20γZ, pH30γZ or pH45γZ. Plasmid pP20γZ was deposited at CNCM [National Collection of Micro-organism Cultures] (Paris, France) on 31 Oct. 1995, registration number I-1640. Plasmid pH45γZ was deposited at the CNCM on 31 Oct. 1995, registration number I-1639.

The scope of the invention also encompasses a polypeptide as expressed by a recombinant nucleotide sequence satisfying the above definitions.

The expression "polypeptide" as used within the context of the invention does not introduce a particular limitation as regards the number of amino acids forming the polypeptide. It may include sequences comprising several amino acids, normally termed peptides, or much longer sequences such as those in proteins.

In this regard, the invention provides lysine-rich modified maize γ-zein, characterized in that it is coded by a recombinant nucleotide sequence as described above.

In a preferred embodiment of the invention, the lysine-enriched modified maize γ-zein is characterized in that its amino acid sequence is modified by at least one polypeptide with formula $(P-K)_n$, where:

n is a whole number of 2 or more;

P represents a proline amino acid residue;

K represents a lysine amino acid residue, the symbol "—" represents a bond between the two amino acid residues, in particular a peptide type bond, the n (P—K) units being bonded together by such bonds, in particular peptide type bonds.

In a variation, the polypeptide integrated in the γ-zein amino acid sequence has the formula $K-(P-K)_n$.

The polypeptides of the invention with one of formulae $(P-K)_n$, $K-(P-K)_n$ or with one of the variations are substituted for a sequence naturally present in the normal maize γ-zein or inserted with deletion of one or more amino acids of the amino acid sequence of normal maize γ-zein, or added to the normal γ-zein amino acid sequence, the insertion site for the polypeptide being selected such that:

when the modified lysine-rich γ-zein is produced in a host cell, in particular in a plant cell, it is localised in that cell in identical or similar manner to normal maize γ-zein which would be produced under the same conditions, in the same host cell; and/or the modified maize γ-zein is recognised by antibodies directed against the normal maize γ-zein.

The P20γZ proteins shown in FIG. 11 (SEQ ID NO:11) or H30γZ or H45γZ shown in FIG. 10 (SEQ ID NO:9) are preferred embodiments of the invention and represent lysine-enriched modified maize γ-zeins.

The invention also provides a recombinant host cell, characterized in that it comprises a nucleotide sequence as described above.

Examples of host cells of interest are bacterial cells, such as *E. Coli* or *Agrobacterium tumefaciens*. Preferably, within the context of the invention and for stable expression of the desired modified protein reserve, host cells of plant origin will be used.

As an example, the cells of plant origin are seed, plant and, for example, as is preferred, maize seed endosperm cells.

The nucleotide sequence of the invention is preferably introduced into the genome of the host cell in a stable manner and under conditions such that the expressed protein reserve which is enriched in amino acids, in particular lysine, is localised as the corresponding normal protein would be in the same host cell.

A variety of techniques are available for transforming host cells. Examples for transforming host cells in a stable or transient manner, electroporation, bombarding with microprojectiles carrying DNA using a particle cannon, explant culture with *Agrobacterium tumefaciens*, by microfibre penetration.

In addition to maize seed endosperm cells, soya, sunflower, tobacco, wheat, oats, alfalfa, rice, oilseed rape, sorghum or *Arabidopsis* cells can be used to express the nucleotide sequences of the invention.

The present application also relates to seeds producing a polypeptide as described above and the plants producing this polypeptide. These plants are preferably maize.

The invention also relates to seeds obtained from transformed plants expressing the polypeptide of the invention, in other words the modified protein reserve enriched with particular amino acids.

In a particularly interesting embodiment of the invention, the modified lysine-enriched γ-zein proteins are expressed in opaque-2 maize mutants. The lysine content of these o2 mutants described by Emerson R. A. et al., (1935, Cornell Univ. Agric. Exp. Stn. Mem. 180) and characterized by Mertz E. T. et al., (1964, Science 145: 279-280) is substantially increased thus greatly increasing the nutritional qualities of the maize (compensating for the its low level of this essential amino acid). Conventional maizes have a lysine content of about 0.24% of the raw product (total grain weight), but opaque-2 maizes have close to 0.5% of lysine. However, they have insufficient agronomic characteristics as their endosperm is far less vitreous and is very friable ("starchy" phenotype). This renders them extremely sensitive to pathogenic organisms and to post harvest treatments. This phenotype is due to a large reduction in certain protein reserves, in particular alpha zeins. In fact, opaque-2 codes for a transcription factor necessary for expression of certain zein genes (Schmidt R. J. et al., 1990, Proc. Natl. Acad. Sci. USA, 87, 46-50).

Opaque-2 derivatives no longer having the disadvantages cited above have been developed by conventional genetic improvement, namely QPM (Quality Protein Maize). Recent genetic analysis of these maizes (Lopes M. A., et al., 1995, Theor. Appl. Genet. 19, 274-281) has shown that only 2 or 3 loci are key loci in these favourable modifications. More detailed genetic and biochemical analyses have resulted in the postulation that one of the 3 loci responsible is the γ-zein locus: maize genotypes which carry a duplicate of this gene located in the centrometric region of chromosome 7 have all been shown to be opaque-2 modifiers (Lopes M. A. et al., 1995, Mol. Gen. Genet. 19: 247: 603-613).

The present invention also enables opaque-2 mutant maizes to be prepared from maize having only one γ-zein gene in chromosome 7, which are complemented by addition of a recombinant sequence coding for a lysine-enriched maize γ-zein. In addition to acquiring hardness properties similar to a non mutant opaque-2 maize, it has the advantage of significantly increasing the lysine content, thus exceeding that of QPM maize.

The present invention enables modified maize opaque-2 mutants to be obtained, into which a recombinant nucleotide sequence coding for a lysine-enriched maize γ-zein has been inserted.

The invention also provides a method of obtaining plants or seeds expressing a modified protein reserve, characterized in that it comprises the steps of:

a) transforming a plant cell, with a nucleotide sequence or a vector as described above, under conditions enabling the modified protein reserve coded by the nucleotide sequence to be expressed in a stable and functional manner;

b) regenerating plants from the plant cell transformed in step a), to obtain plants expressing the modified protein reserve, c) if necessary, obtaining seeds from the modified plants obtained in step b).

In an advantageous implementation of the invention, the transformed plant is maize and the enriched modified protein reserve is lysine-enriched γ-zein.

The invention also relates to plants obtained by carrying out such a method.

In order to evaluate the content of a given amino acid in plants of the invention, it is possible to use an assay protocol such as that described in Zarkadas et al., 1995, J. Agri. Food Chem. Vol. 43: pages 84-93.

Further characteristics and advantages of the invention will become apparent from the following examples and the accompanying figures.

FIG. 1

Restriction map of plasmid pP20γZ;

FIG. 2

Restriction map of plasmid pH45γZ;

FIG. 3

Schematic representation of proteins coded by modified and non modified γ-zein genes: wild type γ-zein (γZ), and lysine-rich γ-zeins (P20γZ (inserted sequence is SEQ ID NO: 3), H30γZ (inserted sequence is SEQ ID NO: 3), H45γZ (inserted sequence is SEQ ID NO: 4) and N13γZ (inserted sequence is SEQ ID NO: 5)) resulting from inserting oligonucleotides coding for lysine-rich sequences. The amino acid sequence of the inserted polypeptides is indicated using the single-letter amino acid designations. The following abbreviations are used:

Term: terminal;

ProX DOMAIN: proline-Xaa linker domain.

Figure 4:
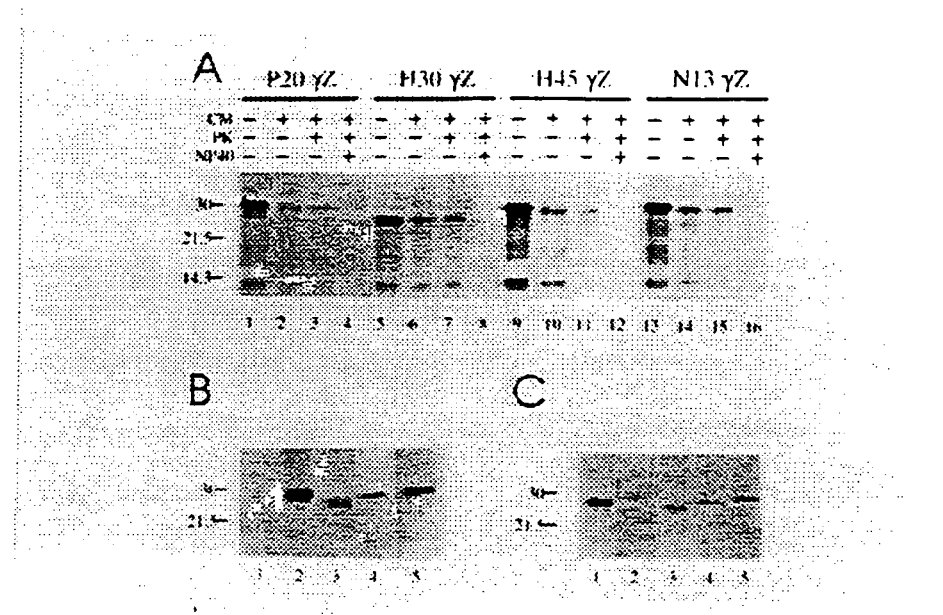

FIG. 4—In-vitro analysis of lysine-rich γ-zeins. (A) in vitro translation and translocation of transcripts corresponding to lysine-rich modified γ-zeins; lines 1, 5, 9 and 13: complete translation products; lines 2, 6, 10 and 14: complete translation products after translocation in canine microsomes (CM), lines 3, 7, 11 and 15: translocation products resistant to the action of proteinase K (PK); lines 4, 8, 12 and 16: totality of translation products after treatment with proteinase K in the presence of 0.5% Nonidet P40 (NP40). (B) Immunoprecipitation of in vitro translation products corresponding to γ-zein proteins and lysine-rich modified γ-zein, using αPL antiserum. Line 1: γ-zein; line 2: P20γZ; line 3: H30γZ; line 4: H45γZ and line 5: N13γZ. (C) Same legend as for (B) but using αG2 antiserum. The molecular weight markers (in kilodaltons) are shown on the left.

Figure 5:
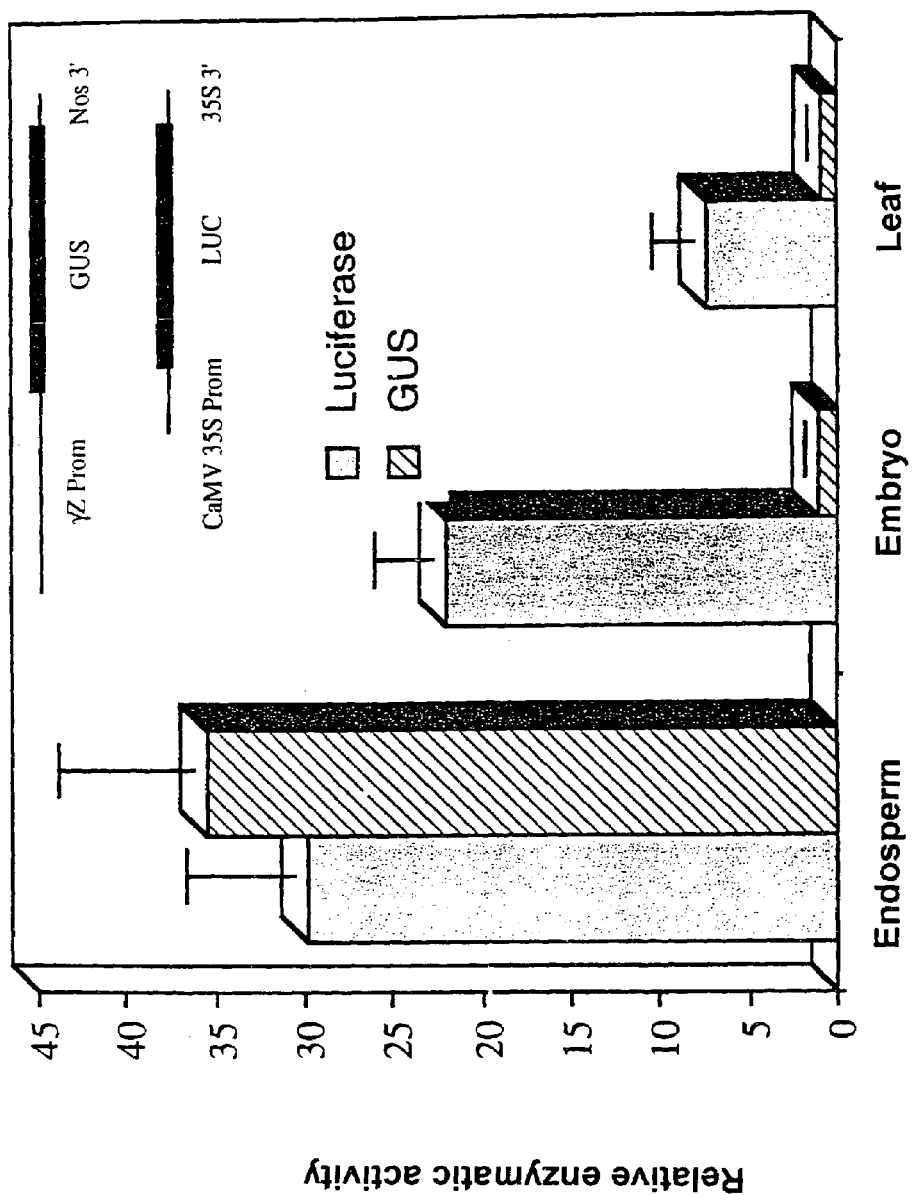

FIG. 5—Tissue-specific activity of the γ-zein promoter. Maize endosperms, embryos and leaves were transformed by bombarding with particles using the constructs represented in the figure (in the right hand portion). The relative activities of luciferase (LUC, grey columns) and β-glucuronidase (GUS, hatched columns) are expressed in the form of a multiplier of the values obtained with naked projectiles±the standard deviation of the different ratios.

Figure 6:
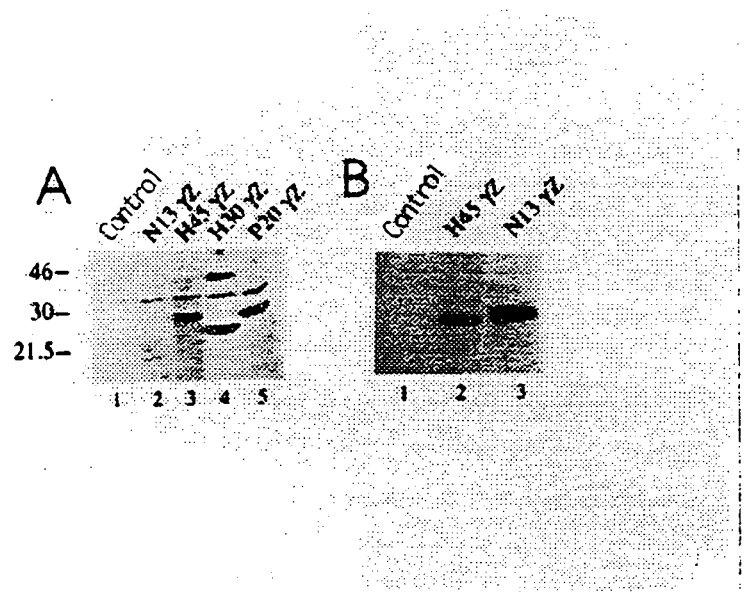

FIG. 6—Expression of lysine-rich γ-zeins in the sub-aleuronic endosperm of cells. (A) Immunoblot with αPL antiserum, of proteins extracted from endosperms transformed by pN13γZ (line 2), pH45γZ (line 3), pH30γZ (line 4) and pP20γZ (line 5). The control (line 1) corresponds to non transformed endosperms. The molecular weight markers (in kilodaltons) are shown on the left hand side. (B) Expression of transcripts H45γZ and N13γZ in transiently transformed endosperms. The cDNAs obtained from tissues transformed with pH45γZ (line 2), pN13γZ (line 3) and the control (line 1) were amplified by PCR and analysed using a synthetic oligonucleotide coding for a lysine-rich sequence used as a probe.

FIG. 7—Accumulation of lysine-rich γ-zeins in the protein bodies of the endosperm. (A) Immunoblot analysis, using αPL antiserum, of protein bodies isolated from endosperms transformed with pP20γZ (line 1), pH30γZ (line 2), pH45γZ (line 3), pN13γZ (line 4) and no DNA (line 5). (B) Immunoblot analysis, using αPL antiserum, of protein bodies isolated from endosperms transformed with pP20γZ, pH30γZ and pH45γZ and digested with proteinase K in the presence of an isotonic buffer (Sugar, lines 1, 3 and 5) or a hypotonic buffer ($H_2O$, lines 2, 4 and 6). The molecular weight markers (in kilodaltons) are shown on the left hand side.

Figure 8:
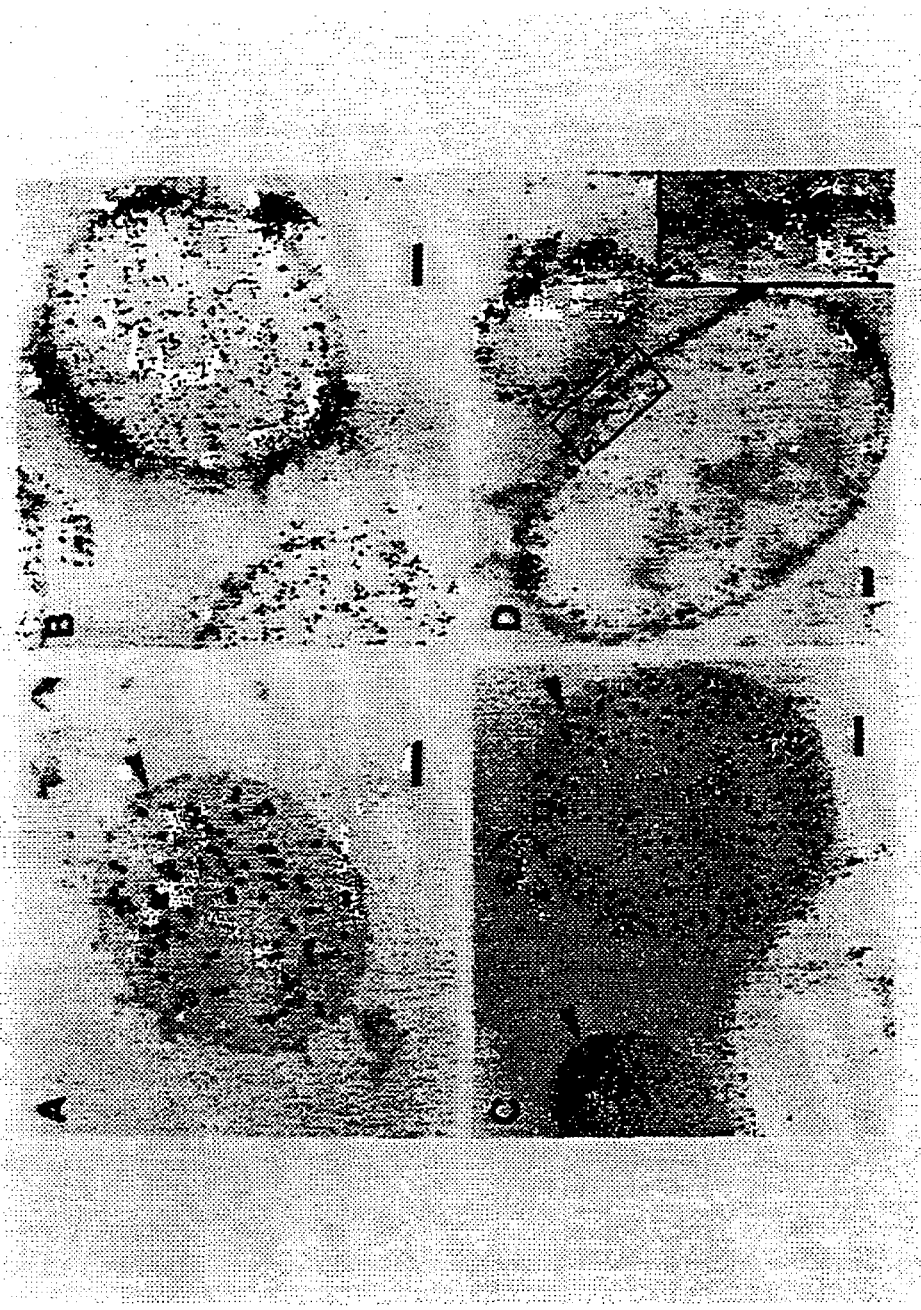

FIG. 8—Co-localisation of P20γZ proteins with α- and γ-zeins in protein bodies of maize endosperm. An immunocytochemical analysis was carried out on ultrafine sections using αPL antibodies (labelled with 15 nm diameter gold particles) and αZ and αG2 antibodies (labelled with 5 nm particles). (A) protein bodies of endosperm transformed with pP20γZ, immunolabelled with αPL antibody. (B) Immunolocalisation of P20γZ (labelled with 15 nm gold particles) and γ-zein (labelled with 5 nm gold particles) in protein bodies isolated from endosperms transformed with pP20γZ. (C) and (D) Immunolocalisation of P20γZ (labelled with 15 nm gold particles) and γ-zeins (labelled with 5 nm gold particles) in protein bodies isolated from endosperms transformed with pP20γZ. The arrows indicate tangential sections of the protein bodies.

FIG. 9—Coding sequence of maize γ-zein cDNA (SEQ ID NO: 6) and the corresponding amino acid sequence (SEQ ID NO: 7).

FIG. 10—Coding sequence of cDNA of the of the H45γZ maize zein (SEQ ID NO:8) and the corresponding amino acid sequence (SEQ ID NO:9).

The lysine-rich sequence (28 amino acids) was introduced between amino acid residues 92 and 119 of the sequence shown in FIG. 10.

FIG. 11—Coding sequence of cDNA of the P20γZ maize (SEQ ID NO:10) and the corresponding amino acid sequence (SEQ ID NO:11).

The lysine-rich sequence (14 amino acids) was introduced between amino acid residues 92 and 119 of the sequence shown in FIG. 11.

Figure 12:
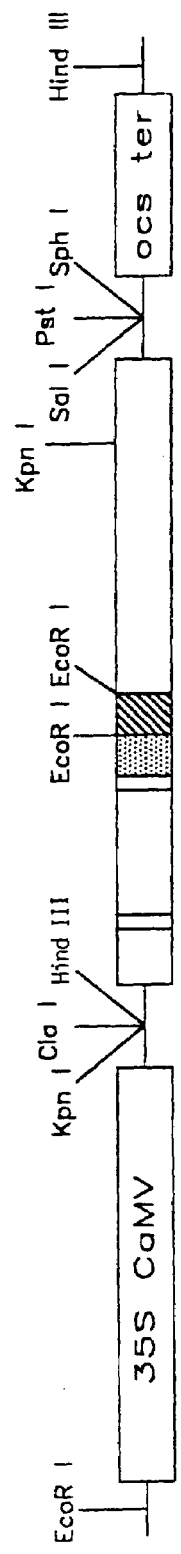
Figure 12:
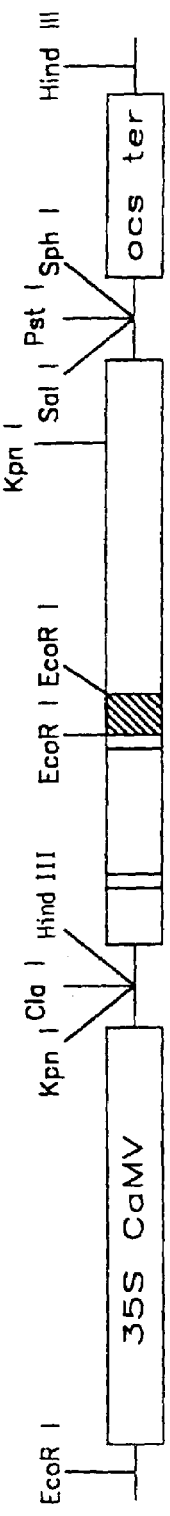

FIG. 12—Restriction maps for plasmids Pbin 19P20γZ and pBin19H30γZ.

Figure 13:
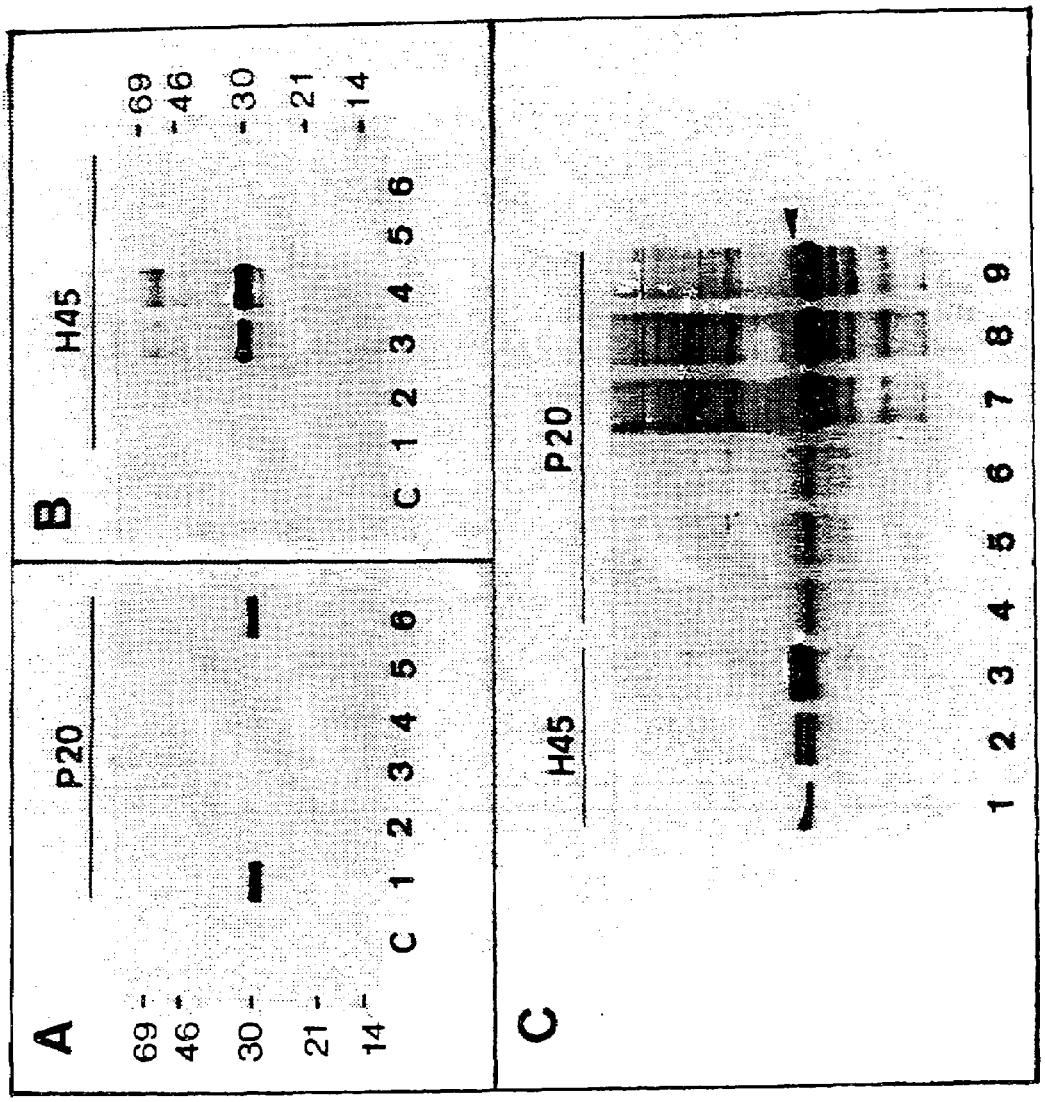

FIG. 13—Transgenic maize plant endosperms accumulating lysine-enriched γ-zein.

A and B: SDS-page and immunoblot using αPL antiserum.

A) 10 μg of protein per track (transformants with construct H45γZ)
track C: protein extract from endosperms
of hybrids B73xA188 (control)
track 1: A1
track 2: B1
track 3: B2
track 4: C1
track 5: D1
track 6: D2

-continued

B) 1 µg of protein per track (transformants with construct P20γZ)
track C: control
track 1: A1
track 2: A2
track 3: B1
track 4: C1
track 5: D1
track 6: E1
C) SDS-PAGE and stain with silver (3 P20γZ transformants and 3 H45γZ transformants)
track 1: A2 ⎤
track 2: B1  |
track 3: C1  |
track 4: B1  } 10 µg of protein per track
track 5: A1  |
track 6: D2 ⎦
track 7: B1 ⎤
track 8: A1  } 40 µg of protein per track
track 9: D2 ⎦

Figure 14:
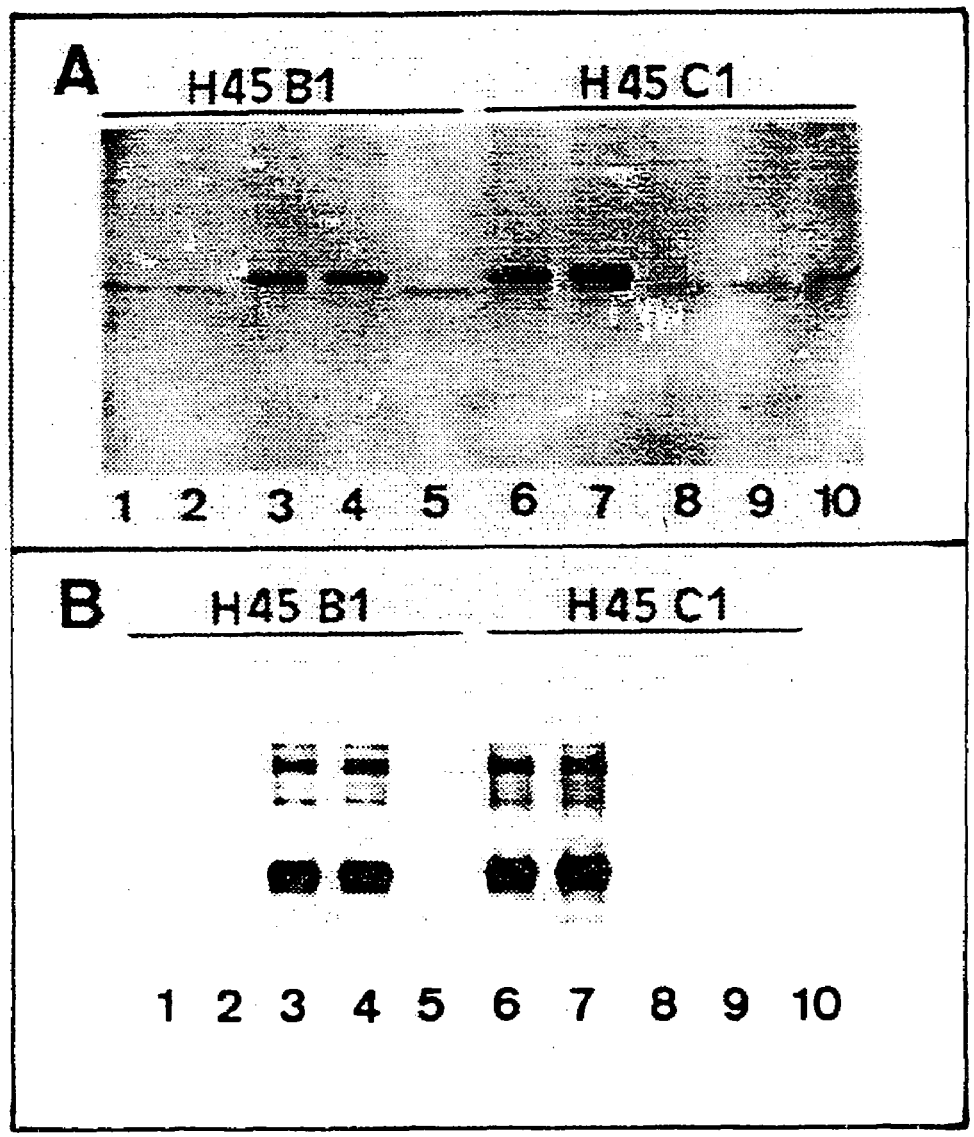

FIG. 14—Lysine-enriched γ-zein content per grain (transformants 45γZ B1 and C1)

A: silver stain; 10 µg of protein per track;

B immunoblot using αPL antiserum; 1 µg of protein per track;

Tracks 1 to 5: protein extracts from different endosperms of transformant 45γZ B1;

Tracks 6 to 10: protein extracts of different endosperms of transformant 45γZ C1.

FIG. 15:

A) Lysine-enriched γ-zein content of 10 grains (transformant 45γZ C1) using αPL antiserum, 1 µg of protein per track;

Tracks 1 to 10: endosperm extract from 10 descendants;

B) Immunoblot of protein extracts of endosperms 1 to 5 present in A) and labelled with αG2 antiserum; 2 µg of protein per track.

EXAMPLES

A) Preparation of Lysine-Enriched Modified γ-zeins and Expression of these Modified Proteins Followed by Accumulation in Protein Bodies of Maize Endosperm Cells γ-zein is a sulphur-rich maize protein reserve, with a molecular weight of 28 kD which is accumulated in endosperm cells with α- and β-zeins, in protein bodies derived from the endoplasmic reticulum (ER) of the grain (Ludevid et al., 1984, Plant Mol. Biol. 3, 227-234; Lending et al., 1984, Plant Cell 1, 1011-1023). The amino acid sequence deduced from the cDNA nucleotide sequence (Prat et al., 1985, Nucl. Acids Res. 13, 1493-1504) and genomic clones (Boronat et al., 1986, Plant Sci. 47, 95-102) show that the γ-zein has no homology with α-zein type polypeptides. While the γ-zein is coded by 1 or 2 genes per haploid genome (Boronat et al., 1986, Plant Sci., 47, 95-102), it represents 10-15% of the totality of the maize endosperm proteins. Expression of the γ-zein gene in heterologous systems such as *Xenopus oocytes* (Torrent et al., 1994, Planta 192, 512-518) and in *Arabidopsis thaliana* (Geli et al., 1994, Plant Cell 6, 1911-1922), indicates that γ-zein polypeptides remain stable and are capable as they are of forming protein bodies derived from the endoplasmic reticulum inside the cells. Further, analyses involving deletion of different structural domains from the γ-zein have shown that the N-terminal sequence including the proline-rich repeat is responsible for retaining the γ-zein in the endoplasmic reticulum and the cysteine-rich C-terminal domain is responsible for forming the protein bodies. The Pro-X domain does not appear to affect the stability of the protein nor its targeted localisation (Geli et al., 1994, Plant Cell 6, 1911-1922).

Material and Methods

Plant Material

After surface sterilisation (1), grains at stage 17 DAP (days after pollination) of W64A maize were dissected by hand and the pericarpal layer and the aleurone were separated from the endosperms. Tangential sections were made to expose a large part of the sub-aleuronic surface. If necessary, embryos were isolated and leaves from 7 day old plants were dissected to extract the epidermal tissue. After dissection, the samples were placed in petri dishes on filter paper moistened with MS medium (Murashige and Skoog, 1962, Physiol. Plant 15, 473-497).

Plasmid Constructs

A first group of plasmids, pKSG2, pHpP2, pPbP4 and pNaN1, was obtained to enable restriction sites to be introduced into the gene coding for γ-zein. pKSG2 and pHbP2 were constructed in accordance with the description in the publication by Torrent et al. (Planta (1994) 192: 512-518). Plasmid pKSG2 contained the sequence coding for γ-zein.

Plasmid pHbP2 was obtained from pKSG2 and contained a sequence coding for a mutated γ-zein from which the Pro-X domain of the protein had been deleted.

Plasmid pPbP4 was obtained following two cloning steps: (I) the restriction fragment SalI-PvuII of 350 kb from pKSG2 was cloned in a Bluescript plasmid (pBSKS, Stratagen, La Jolla, Calif., USA) restricted with SalI and EcoRV (pKSC4) and (ii) the restriction fragment PvuII-XbaI of 600 bp from pKSG2 was cloned in restriction sites SmaI-XbaI of pKSC4. The new construct pPbP4 contained a useful EcoRI restriction site just before the P-X domain of the γ-zein coding sequence.

Plasmid pNaN1 was also obtained following two cloning steps: (i) the NaeI-XbaI fragment of 250 bp from pKSG2 was cloned in the plasmid pBSKS restricted with EcoRV-XbaI (pKSC8) and (ii) the restriction fragment NaeI-HindIII of 700 bp (open ends) from pKSG2 was cloned in the HindIII restriction site of pKSC8. The new construct, pNaN1, contained restriction sites ClaI and HindIII at a position located 15 nucleotides in front of the stop codon for the γ-zein.

Two synthetic nucleotides with the following sequences: SEQ ID No 1: 5'CGATGAATTCAAACCAAAGC-CAAAGCCGAAGCCAAAAGAATTCA3', and the inverse sequence termed SEQ ID No 2, with the following sequence: 5'AGCTTGAATTCTTTTGGCTTCGGCTTTG-GCTTTGGTTTGAATTCAT3' coding for lysine-rich sequences termed (P—K)₄ (SEQ ID NO:13), were hybridised, digested with EcoRI and cloned in an EcoRI site of pHbP2 and pPbP4. Three clones were selected: pPo2 and pHo3 containing the sequence coding for K(P—K)₄ (SEQ ID NO:21) and pHo4 comprising the truncated form of the sequence coding for γ-zein containing a tandem 2K(P—K)₄ (SEQ ID NO:23) (in the form of a sequence K(P—K)₄ EF K(P—K)₄ (SEQ ID NO:24)) of the lysine-rich coding sequence. The same hybridised oligonucleotides were digested with ClaI-HindIII enzymes and cloned in plasmid pNaN1 restricted using the same enzymes. The selected clone, pNo1, contained the sequence coding for the lysine-rich sequence K(P—K)$_4$ (SEQ ID NO:21) at the N-terminal extremity of the corresponding modified γ-zein.

For transient transformation of the endosperm, sequences coding for the modified γ-zein of pPo2 and pHo3 were inserted in the form of HincII-NheI fragments in SmaI-XbaI sites of pDH51 (Pietrzah et al., 1986, Nucl. Acid Res., 14, 5857-5868) containing the 35S promoter of the cauliflower mosaic virus (CaMV). The promoter pP20γZ obtained by the insertion described above of HincII-NheI fragments in plasmid pDH51 contained the coding sequence for lysine-enriched γ-zein (FIG. 8) and signals of the 35S sequence of the CaMV virus for forming the 3' end and polyadenilation. The chimeral coding sequence P20γZ was constructed from the region coding for γ-zein contained in the pKSG2 plasmid after different cloning steps. The 1.7 kb promoter for the γ-zein (Reina et al., 1990, Nucl. Acids Res. 18, 6426) was inserted in the blunt ends of a HindII-PvuI fragment in pH04 and pNo1 restricted with Xh01 and obtained with blunt ends. Constructs pH45γZ and pN13γZ were obtained respectively.

The novel constructs, respectively termed pP20γZ, pH30γZ, pH45γZ and pN13γZ, were used in biolistic bombardment experiments.

To study the specificity of different promoters as regards plant tissues, two constructs, p1.7γZGUS and pCaMV35SLUC were used. p1.7γZGUS was obtained by inserting the 1.7 kb γ-zein promoter (HindIII-PvuI) into a plasmid derived from pPuC18 containing the GUS gene and NOS signals for polyadenilation of pBI 101.1 at 3' (Jefferson et al., 1987, Embo. J. 6, 3901-3907). pCaMV35SLUC was obtained by inserting the gene coding for luciferase (LUC) from pAHC18 (Bruce et al., 1989, P. H. 86, 9692-9696) into the pDH51 polylinker (Pietrzak et al., 1986, Nucl. Acids Res. 18, 6426).

In-Vitro Analysis

The plasmids derived from pBSKS containing the coding sequences for the γ-zein (pKSG2) and lysine-rich γ-zein (pPo2, pHo3, pHo4 and pNo1) were transcribed in vitro using standard protocols (Sambrook et al., Molecular Cloning: A laboratory manual, 2$^{nd}$ edition, Cold Spring Harbor Laboratory ed., Cold Spring Harbor, N.Y.). In vitro translation and translocation of the synthetic transcripts was carried out using the Torrent et al. technique (1994, Planta 192, 512-518), with the exception of the canine microsomes (CM) which originated from Promega (Madison, Wis., USA). The translated products were immunoprecipitated essentially using the Borgese and Gaetani method (1980) using an anti-γ-zeinα-G2 rabbit serum (Ludevid et al., 1985, Plant Sci., 41, 41-48) and an αPL antiserum. αPL is a polyclonal rabbit antiserum obtained against the synthetic peptide EFK(P—K)$_8$EF. This peptide was synthesised using the solid phase synthesis technique described by Celma et al., 1992.

Microprojectile Bombardment

Plasmidic DNA was absorbed onto gold particles (1.0 µm, Bio-Rad, Lab., Richmond, Calif., USA) using a protocol described by Kikkert (Plant Cell, 33: 221-226, 1993). All of the targets were bombarded twice, using a BioRad Biolistic PDS/100/He apparatus. The targets were positioned 8 cm behind a screen stopping macrocarriers, which were positioned 1 cm below a 900 PSI rupture disk. After bombardment, the samples were incubated for 24 hours at 26° C. in the dark. The controls were constituted by targets bombarded with microprojectiles containing no DNA.

Enzymatic Tests

Tissues bombarded with p1.7γZGUS and pCaMV35SLUC plasmids were homogenised over ice in a buffer containing 25 mM of Tris, at a pH of 7.8, 2 mM of DTT, 10% of glycerol and 1% of Triton X-100. After centrifugation at 12000 g for 5 minutes, the supernatants were decanted and the total soluble protein in the extracts was quantified using the Bradford test (Bio-Rad). The GUS activity was tested by fluorimetric analysis following the description by Jefferson (1987) using 4-methyl-ombelliferyl-β-D-glucuronide (MUG) as a substrate. The LUC activity was determined using a Luciferase Assay System Kit sold by Promega, following the manufacturer's instructions.

Extraction of Protein Reserves and Gel Analysis of Proteins

Endosperms transformed with pP20γZ, pH20γZ, pH45γZ and pN13γZ were reduced to flour and the α-zeins were extracted by means of three series of solvents containing 70% of ethanol. The residual flour was air dried, and the total proteins were extracted with a buffer containing 0.25 M of Tris-HCl, pH 6.8, 4% of sodium dodecyl sulphate (SDS) and 5% of 2-mercaptoethanol, for 1 hour at ambient temperature. The protein extracts were analysed by SDS-PAGE and immunoblot following the description by Ludevid et al., 1985. Nitrocellulose leaves were incubated with αPL antiserum (dilution 1:500) and Raifort peroxidase conjugated with a secondary antibody (ECL Western Blotting System, Amersham, Buckinghamshire, UK) was used to detect the protein.

Analysis of RNA Expression

Total RNA was extracted in accordance with the description by Logemas et al., 1987. Complementary DNA (cDNA) was prepared using reverse transcriptase and oligo dT from Gibco BRL (Gaithersburg, Md., USA) following the manufacturer's instructions, and this RNA was amplified using a PCR reaction. Primer oligonucleotides used for the PCR were 20-mer sequences corresponding to the 5' and 3' ends of the γ-zein structure. Standard protocols were used to prepare the $^{32}$P labelled probes, and for gel analysis of the DNA (Sambrook et al., Molecular Cloning: A Laboratory Manual, 2$^{nd}$ ed., Cold Spring Harbor Laboratory Ed., Cold Spring Harbor, N.Y.) using a synthetic oligonucleotide coding for a lysine-rich sequence (see above) as a probe.

Isolation of Protein Bodies and Treatment with Protease

These protocols were described above (Torrent et al., Planta, 180: 90-95, 1989).

Electron Microscopy

The protein bodies of wild type endosperms and endosperms transformed by pP20γZ were fixed with 2.5% of paraformaldehyde in 20 mM of phosphate buffer at pH 7.2, for 1 hour at ambient temperature, and transformed in accordance with the description by Geli et al., 1994, Plant Cell 6, 1911-1922), using, however, a αPL antiserum and a colloid of gold and protein A with a diameter of 15 nm. For double labelling, ultra fine sections were first incubated with αPL and the colloid of gold and protein A (15 nm diameter) was used to detect the antibody. After washing, sections were incubated with 0.15 mg/ml of protein A for 20 minutes to saturate the immunoglobulins and finally the screens were incubated with α-G2 or α-Z1 sera and the gold/protein A colloid (5 nm diameter) was used to detect the antibody. α-Z1 is a polyclonal rabbit antiserum directed against the α-zein obtained following the description by Ludevid et al., 1985, Plant Sci., 41, 41-48.

Results

Construct of Lysine-Rich γ-zeins

The inventors have demonstrated the importance of the proline-rich repeat and the cysteine-rich C-terminal domain for retention of the γ-zein in the endoplasmic reticulum and the formation of protein bodies containing these proteins in the cells of *Arabidopsis* leaves (Geli et al., 1994, Plant Cell 6, 1911-1922). On the basis of these previous results, the possibility of inserting lysine-rich sequences in different domains of the γ-zein, to create a modified γ-zein correctly targeted and accumulated in the endosperm cells, was investigated to improve the nutritional qualities of the maize.

Figure 3:
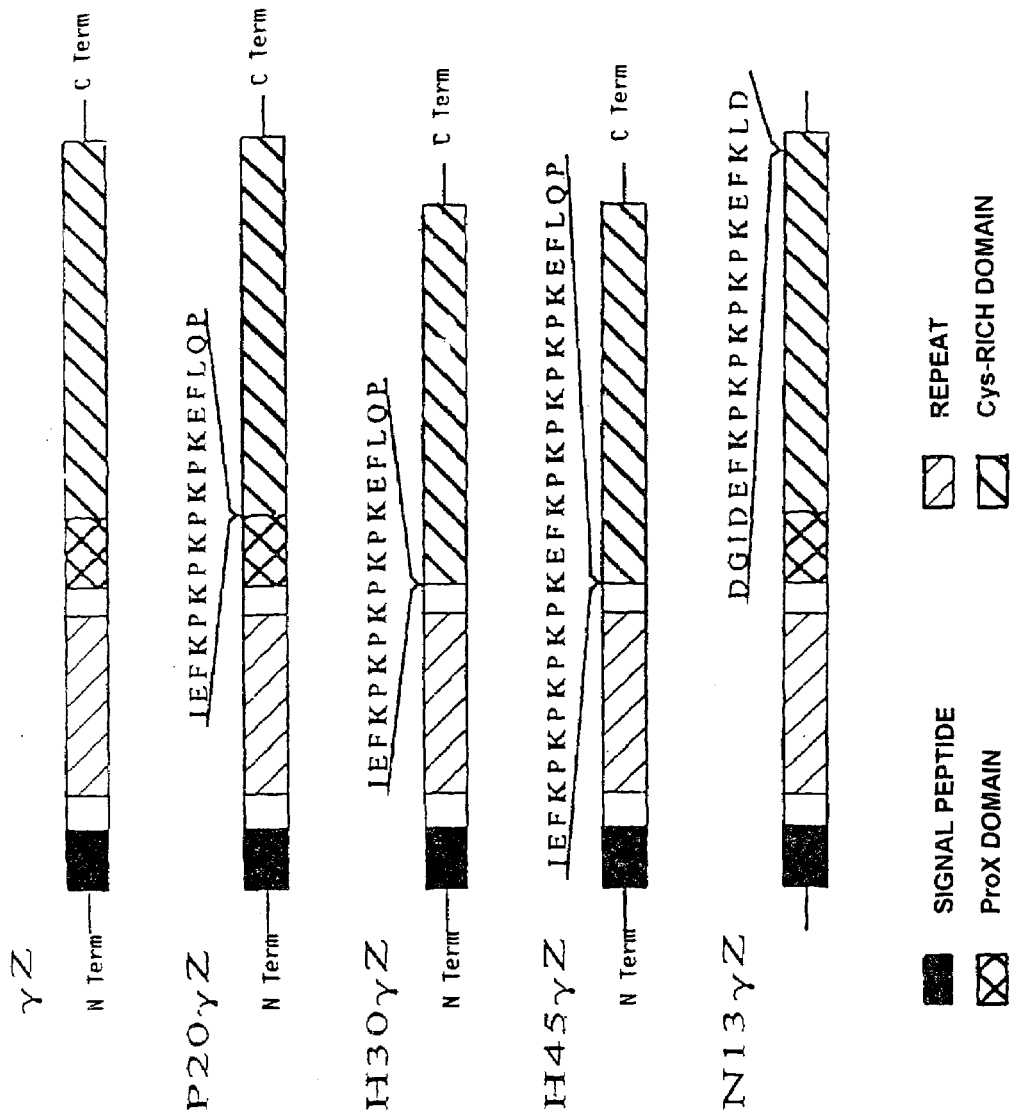

The inventors have now constructed modified γ-zein genes by introducing synthetic oligonucleotides coding for lysine-rich sequences into different sites of the γ-zein coding sequence. Modified γ-zein constructs were created so as to avoid placing lysine-rich coding sequences in domains constituted by the tandem repeat and the cysteine-rich domain. Modifications of the γ-zein coding sequence were made in the sequence corresponding to the Pro-X domain. Further, to minimise any alteration to protein folding, the lysine-rich sequences $(P-K)_n$ were defined to imitate the sequence of the Pro-X domain. As can be seen in FIG. 3, a sequence $K(P-K)_4$ (SEQ ID NO:21) has been introduced into the protein P20γZ after the Pro-X region and in protein H30γZ and in protein H45γZ, amino acid sequences including $K(P-K)_4$ (SEQ ID NO:21) and $2K(P-K)_4$ (SEQ ID NO:23) (in the form of a sequence $K(P-K)_4$ EF $K(P-K)_4$ (SEQ ID NO:24)) respectively replace the Pro-X domain of the γ-zein (γZ, FIG. 3). To study whether the C-terminal extremity was a neutral site for the introduction of lysine-rich sequences, a supplemental N13γZ protein was created by inserting a sequence containing $K(P-K)_4$ (SEQ ID NO:21) five amino acids upstream of the C-terminal extremity (FIG. 3).

Activity of the γ-zein Promoter in Transformed Maize Endosperm

To determine whether lysine-rich γ-zeins could be expressed in endosperm cells, an efficient promoter and a transformation system were researched in the first instance. A γ-zein promoter containing an upstream 1.7 kb sequence (Reina et al., 1990, Nucleic Acid Research, vol. 18, p 6426) and the CaMV promoter containing 625 bp of the sequence upstream of the 35S protein of the cauliflower mosaic virus CaMV were tested. Until now, no information has been available on the functional analysis of gene fusions with the γ-zein promoter in transgenic monocotyledonous plants. To analyse the activity and tissue specificity of the γ-zein promoter, two chimeral genes were constructed (see FIG. 5).

Transient expression by biolistic bombardment (Klein et al., 1988 PNAS 85: 4305) was used as the maize transformation procedure to analyse the promoter and for lysine-rich γ-zein expression experiments. Maize endosperms at the 17 DAP (days after pollination) stage (the pericarp and the cells of the aleuronic layer were removed), embryos (17 DAP) and young leaves (10 days old) were bombarded with gold projectiles coated with plasmidic DNA containing the two constructs. FIG. 5 shows the β-glucuronidase (GUS) activities and luciferase (LUC) activities present in the three tissues tested: endosperm, embryo and leaf, with respect to the control experiment. It should be noted that the results correspond to the average of at least 3 independent experiments carried out. All GUC activity under the control of the γ-zein promoter was restricted to the endosperm, since no GUS expression was detected in the embryo and in the leaves. Further, the bombarded endosperms were histochemically stained to determine the number of cell clusters expressing the GUS protein. The stain profile corroborated the above results, GUS being strongly expressed in the endosperms (the average number of GUS stained clusters per endosperm was 150) and blue spots were not detected in the embryo and in the leaves. In contrast, the promoter CaMV35S conferred a LUC activity on all of the tissues tested (FIG. 5), but there were quantitative differences between the relative activity of the enzyme in the leaves and the embryos with respect to the endosperm. These differences could be attributed to an intrinsic variability in the constitutive activity of the CaMV promoter between the different maize tissues or to low penetration of DNA-coated particles into the mesophyll cells containing a large vesicular system. The prior art contains tests in which the CaMV promoter normally has low activity in monocotyledonous plant cells (Fromm et al., 1985, Proc. Natl. Acad. Sci. USA 82, 5824-5828); however, the inventors have demonstrated a high activity of the CaMV promoter in endosperm cells. This prompts the conclusion that the activity of the γ-zein promoter and the CaMV35S promoter was very high in maize endosperms and thus the two promoters could be useful in controlling expression of the protein in this tissue.

In order to determine if the mutant proteins coded by the constructs were competent with the membrane translocation function, in-vitro transcription-translation experiments were carried out in the presence of dog pancreatic microsomes. The synthetic transcripts of each construct were translated and translocation through the microsome membranes was tested by examining the protection as regards the digestion with K proteinase. These results, shown in FIG. 4A, indicate that the apparent molecular weights of in-vitro synthesised polypeptides reflect the mutations introduced (FIG. 4A, lines 1, 5, 9 and 13). In the presence of microsomes and the K proteinase, low molecular weight peptides were not observed, indicating that the complete polypeptide chains of the modified γ-zeins were transported through the microsomal membranes (FIG. 4A, lines 3, 7, 11 and 15). By comparing the result of translocation of the four modified γ-zeins, it can be seen that protein H45γZ (FIG. 4A, line 11), which contained the 10 lysine type amino acid insertion, had undergone less translocation than the other proteins. It appears that negatively charged residues could interfere to a certain extent with translocation efficiency. Since the polyclonal antibody αG2, directed against γ-zein (Ludevid et al., 1985, Plant Sci. 41, 41-48) could not be used to distinguish between the wild type γ-zein and modified γ-zeins, an αPL antibody directed against a synthetic peptide containing the lysine-rich amino acid sequence was prepared. It was then tested to examine whether the modified proteins synthesised in vitro were recognised both by the αG2 antibodies and the αPL antibodies. This experiment is illustrated in FIG. 4B and FIG. 4C where the synthetic transcripts of the γ-zein, P20γZ, H30γZ, H45γZ and N13γZ, were translated in-vitro and in which the translation products were immunoprecipitated with αPL (FIG. 4B) and with αG2 (FIG. 4C). These results indicate that lysine-rich γ-zeins were recognised by the two antibodies (see FIGS. 4B and C, lines 2 to 5) and that the γ-zein was only recognised by the αG2 serum (FIGS. 4B and C, line 1). Thus the specificity of the antibodies αPL for the modified proteins enabled the lysine-rich γ-zein to be distinguished from the endogenic γ-zein when the modified genes were expressed in endosperm cells. Taken together, these experiments have shown that the presence of lysine-rich sequences did not disturb the function of translocation through the membrane or the immunological behaviour of the γ-zein.

Analysis of Expression of Lysine-Enriched γ-zeins in Maize Endosperms

To explore whether lysine-rich modified γ-zein was expressed and accumulated in endosperm cells, stage 17 DAP grains were bombarded with DNA containing sequences coding for the protein of the four constructs (FIG. 3) under the control of the CaMV promoter (P20γZ and H20γZ) and the γ-zein promoter (H45γZ and N13γZ). Constructs including antisense promoters or free of promoters were used as controls. After 24 hours of endosperm transformation, the total proteins were extracted and the expression of modified γ-zein was tested by immunoblotting using the αPL antibody. FIG. 6A shows that the chimeral genes of γ-zein containing the (Pro-Lys)$_n$ insertion after the Pro-X domain (P20γZ) or replacing it (H45γZ and H30γZ) were strongly expressed and the translation products accumulated efficiently in the endosperm cells (FIG. 6A, lines 3, 4 and 5). For each line, the protein extracts corresponded to about ⅓ of one bombarded endosperm, enabling it to be estimated that the quantity of modified proteins P20γZ, H30γZ and H45γZ per endosperm reached a nanogram level. Further, no quantitative difference between the level of expression of chimeral genes under the control of the CaMV promoter and the γ-zein promoter was observed, confirming the results described above obtained with reporter proteins GUS and LUC (FIG. 5). It should be noted that the αPL antibody recognised a protein of about 30 kD present in the total protein extracts, even in non transformed endosperms (see the weak band present in the four lines of FIG. 6A). A sequential protein extraction procedure established that this protein was not a protein reserve which was soluble in an aqueous medium.

FIG. 6A (line 2) shows that no trace of the N13γZ protein could be detected, indicating that the corresponding chimeral gene was not expressed in the endosperm cells or that the N13γZ protein had degraded. The RNAs of endosperms transformed with the DNAs coding for the H45γZ and N13γZ proteins and the RNAs of non transformed endosperms were analysed. From the total RNAs, the cDNAs were prepared and amplified by PCR using specific primers. FIG. 6B shows the Southern blot analysis of three cDNA samples hybridised with an oligonucleotide coding for a sequence K(Pro-Lys)$_4$ (SEQ ID NO:21) used as a probe. The results indicated that the N13γZ gene was correctly expressed (FIG. 6B, line 3). The presence of bands in the H45γZ and N13γZ samples but not in the non transformed endosperms, has suggested that the N13γZ protein was degraded during the 24 hours of incubation.

From these observations, the inventors have concluded that the insertion site for lysine-rich sequences was critical for the stability of the modified γ-zein.

Lysine-Enriched γ-zein is Accumulated in Protein Bodies

Apart from the lysine content in the Pro-X sequences, the P20γZ, H30γZ and H45γZ proteins had common characteristics with the wild type γ-zein: they had the signal peptide, the N-terminal tandem repeat and the cysteine-rich C-terminal region in common. It appeared important to determine whether these domains remained completely functional preserving targeting and formation of the protein bodies or whether the lysine-rich sequences created a special environment in which these properties could be perturbed. To test this, an investigation was made as to whether the modified γ-zeins were capable of accumulating in protein bodies. A sub-cellular fractionation was carried out with transformed endosperms. Homogenates of bombarded endosperms were charged onto discontinuous sucrose gradients (20%, 50% and 70% of sucrose) and all of the fractions collected were analysed by immunoblotting. P20γZ, H30γZ and H45γZ sedimented on the protein body fraction and no significant quantity of these proteins was detected either in the supernatant or in the microsomal fraction (FIG. 7A, lines 2, 2 and 3). While the in-vitro experiments previously carried out (FIG. 4A) had established that the newly synthesised modified γ-zeins underwent translocation in canine microsomes, the test in this case was whether the modified proteins expressed in-vivo in endosperm cells underwent translocation in the membrane of the endoplasmic reticulum and remained inside protein bodies derived from the endoplasmic reticulum. For this reason, isolated protein bodies were digested with K proteinase in isotonic buffers (containing 20% of sucrose) or after an osmotic shock in water (FIG. 7B). Proteins protected against proteolytic degradation by enzymes can be surrounded by a membrane and treatment with detergent or hypotonic solutions results in digestion of the proteins (Walter and Blobel, 1983, Method Enzymol. 96, 84-93). A comparison of the band intensities after digestion with K proteinase in media comprising sucrose or water revealed that the P20γZ, H30γZ and H45γZ proteins were protected from digestion in isotonic buffers (lines 1, 3 and 5) but were partially digested in water (lines 2, 4 and 6).

Expression of modified genes of γ-zein in the cells of the sub-aleuronic layer of the endosperm by biolistic bombardment resulted in the observation that lysine-rich γ-zeins were accumulated to a great extent with the exception of the case where the lysine-rich sequences were positioned 5 residues upstream of the C-terminal extremity of the γ-zein polypeptide. From this expression and immunocytochemical studies on isolated protein bodies, the inventors have demonstrated that lysine-rich γ-zeins are properly accumulated in these organelles and are co-localised with the endogenous γ-zein and α-zein proteins.

Protein bodies isolated from P20γZ endosperms were examined by immunogold type labelling and electron microscopy. On ultra fine sections incubated with the αPL antibody (FIG. 8A), the gold labelling was detected inside the protein bodies, indicating that the lysine-rich protein P20γZ was accumulated inside these organelles. In sections incubated only with αPL antibody, immunolabeling took place only on some protein bodies (containing lysine-rich γ-zein), the large proportion of the isolated protein bodies were not immunolabelled with αPL antibodies as they corresponded to non transformed endosperm cells. To determine whether the lysine-rich γ-zein was co-localised with the α-zeins and γ-zeins, a double labelling using immuno-electron microscopy was carried out on isolated protein bodies using the αZ and αPL antibodies (FIG. 8B) and αG2 and αPL antibodies (FIGS. 8C and D). FIG. 8B shows a micrograph of the transverse section of two protein bodies labelled with αPL antibody (15 nm gold particle) and with the αZ antibody (5 nm gold particle). The result of immunostaining showed that the P20γZ protein was accumulated in the protein bodies and co-localised with the α-zein (see the extent of labelling of the α-zein over the whole surface of the protein body). Further, tangential sections (FIG. 8B, see arrows) and transverse sections (FIG. 8D) of protein bodies were incubated with the αPL antibody (15 nm gold particle) and with the αG2 antibody (5 nm gold particle). In the two cases, the P20γZ protein was co-localised with the γ-zein polypeptides. It was noted that the tangential sections of the protein body (FIGS. 8A, C see arrows), was easily distinguished from the transverse sections of the protein body in that the former had a higher electron density and the γ-zein labelling extended over the whole section. In contrast, the transverse sections had a lower density and the γ-zein labelling was localised on the membrane surrounding the protein body. In both cases, the labelling localisation of the lysine-rich γ-zein followed that of the endogenous γ-zein.

B) Preparation of Genetically Modified Plants Expressing Lysine-Rich γ-zeins

1) Production and Use of Maize Callus as a Target for Genetic Transformation

Genetic transformation of maize, regardless of the method used (electroporation; *Agrobacterium*, microfibres, particle cannon) generally requires the use of undifferentiated cells in rapid division which have conserved an ability to regenerate whole plants. This type of cell constitutes the embryogenic friable callus (type II) of maize.

These calli were obtained from immature embryos of the Hi II or (A188×B73) genotype using the method and media described by Armstrong (Maize Handbook; (1994) M. Freeling, V. Walbot Eds; pp 665-671). The calli obtained were multiplied and maintained by successive subculturing every fortnight onto the initiation medium.

Plantlets were then regenerated from these calli by modifying the hormonal and osmotic balance using the method described by Vain et al., (Plant cell Tissue and Organ Culture (1989 18: 143-151). These plants were then acclimatised under glass where they could be crossed or self-fertilised.

2) Use of Particle Cannon for Genetic Transformation of Maize

The above paragraph described the production and regeneration of cell lines necessary for transformation; this section describes a genetic transformation method leading to stable integration of modified genes into the plant genome. This method is based on the use of a particle cannon identical to that described by J. Finer (Plant Cell Report (1992) 11: 323-328); the target cells were fragments of calli described in paragraph 1. 4 hours before bombardment these fragments, with a surface area of 10 to 20 mm$^2$, were disposed, in an amount of 16 fragments per dish in the centre of a petri dish containing a culture medium identical to the initiation medium, with an addition of 0.2 M of mannitol+ 0.2 M of sorbitol. Plasmids carrying the genes to be introduced were purified on a Qiagen® column in accordance with the manufacturer's instructions. They were then precipitated onto tungsten particles (M10) following the protocol described by Klein (Nature (1987) 327: 70-73). The coated particles were projected against the target cells using a cannon and following the protocol described by J. Finer (Plant Cell Report (1992) 11: 323-328).

The bombarded dishes of calli were then sealed with Scellofrais® then cultivated at 27° C. in the dark. The first subculture took place 24 h later then every fortnight for 3 months to a medium identical to the initiation medium with a selective agent added, the nature and concentration of which could be varied depending on the gene used (see paragraph 3). The selective agents which could be used generally consisted of active compounds of certain herbicides (Basta®, Round Up®) or certain antibiotics (Hygromycin, Kanamycin . . . ).

After three months or sometimes earlier, calli were obtained the growth of which was not inhibited by the selective agent, normally and mainly composed of cells resulting from division of a cell which had integrated one or more copies of the selection gene into its genotype. The frequency of producing such calli was about 0.8 calli per bombarded dish.

These calli were identified, individualised, amplified then cultivated so as to regenerate plantlets (see paragraph 1). In order to avoid any interference with non transformed cells, all of these operations were carried out on culture media containing the selective agent.

The regenerated plants were acclimatised then cultivated under glass where they could by crossed or self-fertilised.

3) Use of Bar Gene to Produce Genetically Modified Maize Plants which Have Incorporated and which Express the H45γZ Gene The bar gene from *Streptomyces hygroscopicus* codes for a phosphinothricin acetyl transferase (PAT) which inactivates the active phosphinothricin molecule of the herbicide Basta® by acetylation. Cells with this gene are thus rendered resistant to this herbicide and can be selected by using it. For the cereal transformation, the coding sequence of the bar gene is under the control of a regulating region enabling strong and constitutive expression in plant cells. Such a region is advantageously constituted by the promoter and the first intron of the actin gene of rice as described by McElroy (Mol. Gen. Genet. (1991) 231: 150-160).

This chimeral gene is cloned on a plasmid enabling its amplification by *Escherischi Coli*. After amplification then purification on a Qiagen® column, this plasmid (pDM 302 Cao (Plant Cell Report (1992) 11: 586-591) can be used for genetic transformation of maize using, for example, the method described in the previous example. In this case, 2 mg/L of phosphinothricin was added to culture media intended to select transformed cells.

To introduce the H45γZ gene, a co-transformation technique is advantageously used: the selection gene (bar) and gene of interest (H45γZ) were carried by independent plasmids. When using a particle cannon, the plasmids were co-precipitated onto tungsten particles, the total quantity of DNA precipitated on the particles remaining identical to that used in the standard protocol (5 μg of DNA per 2.5 mg of particles), each plasmid representing about half of the total weight of DNA used.

The experiment shows that with this method, co-integration of the plasmids in the plant cells is the most frequent event (of the order of 90%) i.e., practically every plant which had integrated the bar gene and been selected by its use also carried the H45γZ gene. The level of co-expression (percentage of selected plants expressing the H45γZ gene) was normally of the order of 70%.

The genes thus introduced were generally linked in the genetic sense, thus gene H45γZ could advantageously be followed through its descendants because of its resistance to the herbicide closely associated with it.

The quantity of modified protein was determined using the methods described in Example A, in particular by immunoblotting onto protein extracts from immature or mature maize grains, removed as a pool from plants resistant to Basta®.

4) Example Explaining the Step of Introducing Transgenes, in Particular the Gene Coding for H45γZ, to Modify the Maize Opaque-2 Phenotype Improving opaque-2 maize by introgression of the lysine-rich γ-zein.

Transformed plants described in the previous example, with both a resistance to Basta and expressing a lysine-rich γ-zein, were used. Their pollen was used to fertilise opaque-2 maize plants from the W64Ao2 line which contained only a single γ-zein gene. This line was obtained from the Maize Stock Center. The plants and its F1 descendants were selected for their resistance to Basta and then self-fertilised. The F2 grains produced were analysed for the opaque phenotype on a light table and opaque or vitreous grains were sown and evaluated for Basta resistance. In the case when opaque grains are sensitive to Basta, introduction of the lysine-enriched γ-zein into the plant under consideration has been demonstrated to complement the opaque-2 phenotype.

In these Basta resistant plants, o2/o2 genotype individuals with only one γ-zein gene on chromosome 7 were selected using molecular probes coding for the opaque-2 gene and for the γ-zein. These latter revealed polymorphic restriction fragments and only individuals with the patron type of the W64o2 line were retained (Lopes M. A. et al., 1995, Mol. Gen. Genet. 19: 247, 603-613).

These individuals had a lysine content which was on average equivalent to or greater than that of o2 maize. From these individuals, any introgression in ELITE varieties, with a "high lysine content" character was observed by determining the resistance to BASTA and the presence of the o2 allelle detected by RFLP.

5) Expression of Lysine-Enriched γ-zeins in *Arabidopsis thaliana*

In order to obtain stable transformation, plasmid constructs P20γZ and pH30γZ cloned in the Bluescript KS (−) plasmid were inserted in the form of HincII/Xbal fragments in the binary vector pBin19 (Bevan, M. Nucl. Acids Res. 12: 8711-8721 (1984)), containing the 35S promoter of the cauliflower mosaic virus (CaMV) and formation signals for the 3' end and polyadenylation of the octopine synthetase gene (ocs). The new plasmids were termed p19P20γZ and p19H30γZ (FIG. 12).

The binary vectors containing the sequences coding for the proteins P20γZ and H30γZ (p19P20γZ and p19H30γZ) were transferred to the LBA4404 strain of *Agrobacterium tumefaciens*. Ecotype RLD *Arabidopsis* plants were transformed using the method described by Valvekens D., Van Montagu, M and van Lijsebettens, M. ((1988) Proc. Natl. Acad. Sci. USA 85: 5536-5540). For each construct, 10 transgenic plants were screened by immunoblot analysis using an antiserum obtained against the γ-zein (αG2, Ludevid et al. 1985). The plants containing the highest amounts (corresponding to about 0.1% of the total quantity of proteins present in *Arabidopsis* leaves) of the transgenic products in generation F1 were selected to obtain generation F2. These plants were also selected for expression of the desired protein.

Whole transgenic plants, selected in a medium containing kanamycin, were homogenised in liquid nitrogen. The transgenic proteins were selectively extracted with a solution containing ethanol/0.125 N hydrochloric acid HCl in a proportion of 3:1 (v/v) with 5% of mercaptoethanol and protease inhibitors. The proteins extracted with this solution were precipitated in 5 volumes of acetone and analysed by SDS-PAGE and immunoblotting. The protein extracts from non transgenic plants were used as controls. The proteins resulting from insertion of K(P—K)$_4$ (SEQ ID NO:21) sequences in the γ-zein were properly expressed in *Arabidopsis thaliana* plants using the constitutive promoter 35S from CaMV. On the immunoblots, antibodies αG2 and αPL recognised electrophoresis bands corresponding to proteins P20γZ and H30γZ. These bands migrated with apparent molecular weights in accordance with those which were previously observed in the in-vitro translation/translocation experiments (30 kD and 26 kD respectively). As observed in the transgenic *Arabidopsis* plants expressing γ-zein (Geli et al., Plant Cell 6: 1911-1922 (1994)), the proteins P20γZ and H30γZ migrated in the form of two electrophoresis bands, namely the bands corresponding to 36 and 30 kD for P20γZ and the bands corresponding to 32 and 26 kD for H30γZ. The higher bands could correspond to products which have undergone post-translational modifications. Such a post-translational modification was not detected in the transformed maize endosperms. This result suggests that the modification would appear when these proteins are expressed in a heterologous system such as *Arabidopsis thaliana*.

6) Expression of Recombinant Lysine-Enriched γ-zeins in Maize

Method

After obtaining transgenic plants, they were crossed with a non transformed male line. As a result, 50% of the grain harvested in the case of unilocus insertion will be transgenic. With the aim of analysing the lysine-enriched γ-zeins in the transgenic plants, the proteins were extracted from 6 grains per transformant.

The endosperms were dissected by removing the embryos and pericarps from the grains. The endosperms were ground and 50 mg of flour was used for selective extraction. Previously the α-zeins were extracted by three treatments with 70% ethanol. After centrifugation, the ethanol was vacuum evaporated. The proteins which were insoluble in ethanol (principally the γ-zeins and lysine-enriched γ-zeins) were extracted from the residue with a Laemli buffer containing 10% of mercaptoethanol (100 μl of buffer per 10 mg of flour). The total proteins were then analysed by staining with silver (Morrissey, J. H. 1981. Ann. Biochem. Vol. 117, p 307-310). The γ-zeins and lysine-enriched γ-zeins were analysed by immunoblot using αG2 (dilution 1/2000) and αPL (dilution 1/500) antibodies respectively. An anti-rabbit antibody conjugated with alkaline phosphatase was used as the secondary antibody in the immunoblot. The extracts were diluted to enable them to be charged onto SDS-PAGE in accordance with the analytical method used.

Results

Accumulation of Lysine-Enriched γ-zein in Transgenic 20γZ and 45γZ Maize Plants FIG. 13 shows an immunoblot of protein extracts revealed with the αPL antiserum (A, B) and the total proteins after silver staining (C). As can be seen in FIG. 13A, 6 20γZ transgenic plants were tested with the αPL antiserum and the lysine-enriched γ-zein was expressed in transgenic plants A1 and D2 (tracks 1 and 6 respectively). In plant C1 (track 4), only traces of lysine-enriched γ-zein were observed. When the extracts from 6 transgenic 45γZ plants were charged onto gel and labelled with αPL antiserum (FIG. 13B), a strong reaction with the antibody was observed for transformants B1 and C1 (tracks 3 and 4 respectively).

It should be noted that the reaction with the antibody in the extracts from endosperms from plants 45γZ B1 and C1 was stronger than in the extracts from plants 20γZ A1 and D2. This result was confirmed after staining the gels with silver (FIG. 13C) where the 2 types of γ-zein: endogenic and lysine-enriched, are stained. The lysine-enriched γ-zein had an apparent molecular weight of 30 kDa and that of the endogenous γ-zein was 28 kDa. Expression of lysine-enriched γ-zein was weaker in the 45γZ B1 plant than in the C1 (tracks 2 and 3 respectively). In tracks 1 to 6 of FIG. 13C, an identical dilution of the proteins from endosperm extracts of plants 45γZ and 20γZ were deposited on the gel. At this dilution, expression of the lysine-enriched γ-zein was detected only in endosperms from plants 45γZ B1 and C1. However, when a larger extract (40 μg of proteins per track) of 20γZ proteins was charged onto the gel, a faint band (see arrow) corresponding to the lysine-enriched γ-zein was detected in endosperms 20γZ A1 and D2. This result indicates that 45γZ plants accumulate many more proteins of the invention than P20γZ plants. This is probably due to the different activities of the promoters. 45γZ plants were transformed with a construct containing the γ-zein of the invention under the control of the γ-zein promoter (1.7 kb) while 20γZ plants were transformed with the same coding sequence but under the control of the CaMV 35S promoter. Silver staining is a general protein staining technique, but the strong brown colour is especially observed in the presence of basic proteins. Since the α-zeins had been extracted from the flour as described above, they were absent during the SDS-PAGE analysis of FIG. 13C.

Segregation

Figure 2:
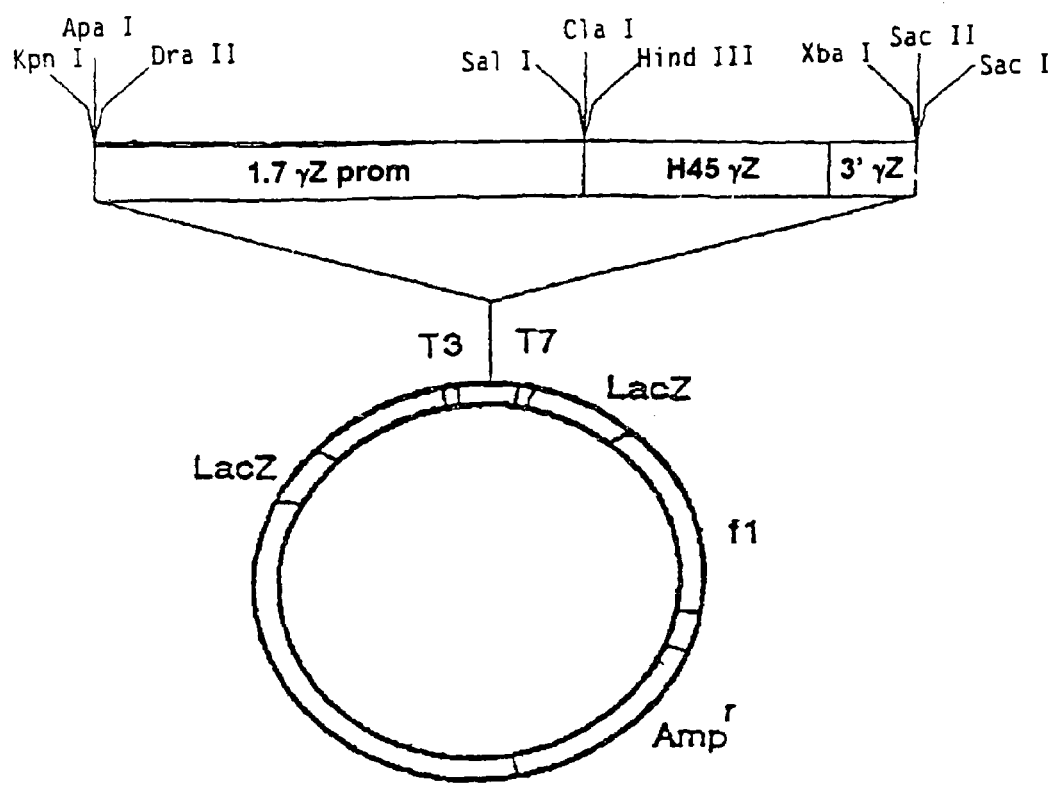
Figure 15:
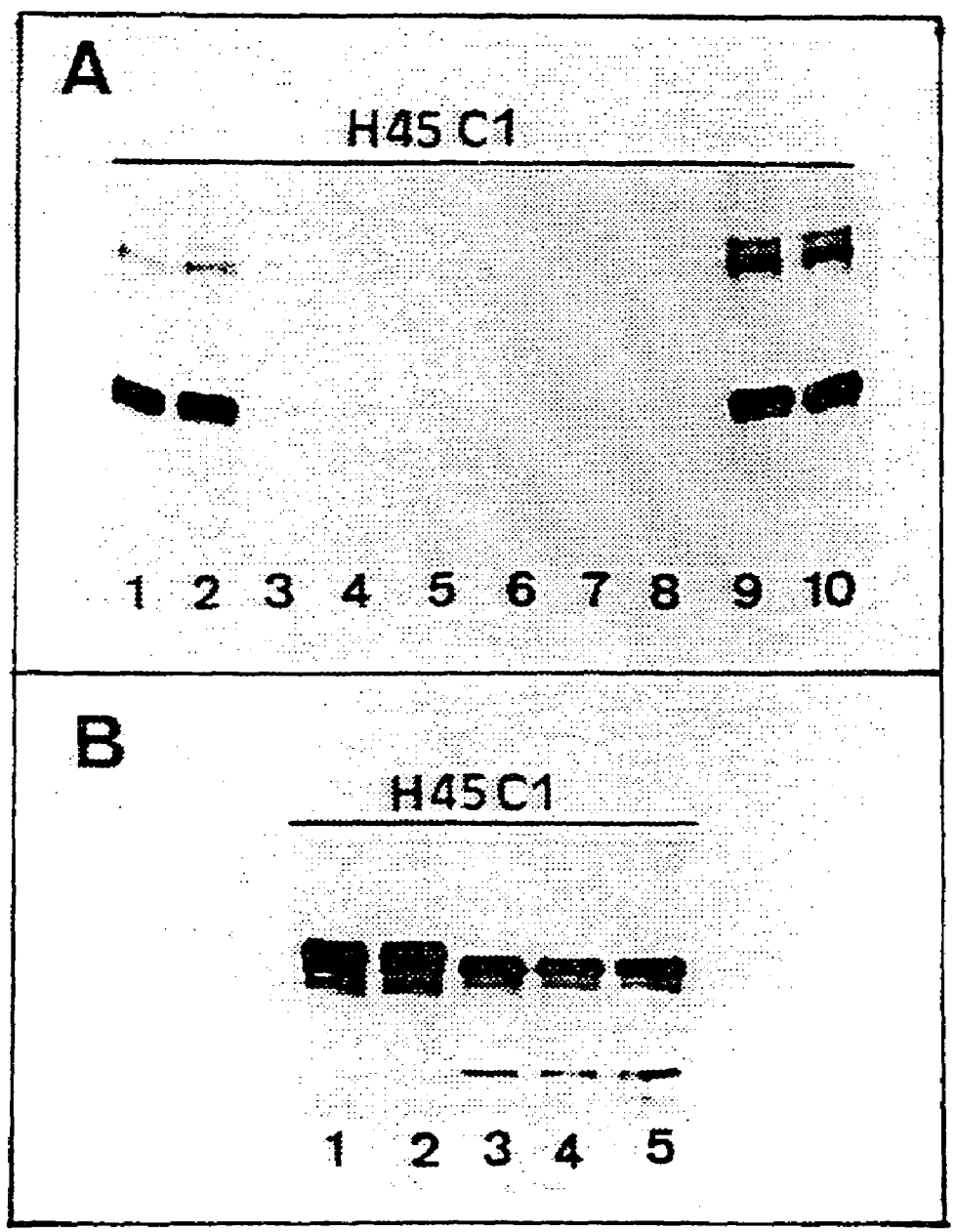

Since there is 50% segregation in all transgenic plants in the case of a single locus, grain by grain analysis was carried out to quantify the amount of lysine-enriched γ-zein in each transformant. The analysis was carried out only with 45γZ transformants which had a stronger degree of expression. FIG. 14 shows the silver staining (A) and immunoblot with αPL (B) of 5 different endosperms of 45γZ B1 and C1. The faint electrophoretic band present on all tracks (see A, tracks 1 to 10) correspond to the endogenic γ-zein. As can be seen in FIG. 14A, 2 of the 5 endosperms accumulated lysine-enriched γ-zein (see tracks 3, 4 and 6, 7). As a result, about half of the grains accumulated significant quantities of lysine-enriched proteins. If the fact that identical quantities of proteins were deposited on the gel was taken into account, it is observed that 45γZ C1 transformant had accumulated more lysine-enriched γ-zein than B1. In fact this result was in agreement with that observed for silver staining of extracts mixed with endosperm (FIG. 13 C, track 3). The proof of the presence of lysine-enriched γ-zein in these endosperms is underlined in FIG. 14B. The immunoblot using the αPL antiserum shows that 2 endosperm extracts of 45γZ B1 (tracks 3 and 4) and 45γZ C1 (tracks 4 and 6) accumulated lysine-enriched γ-zein. To confirm this percentage of transgenic grains, 10 new grains of 45γZ C1 transformant were analysed by immunoblot and using αPL antiserum (FIG. 15A). As expected, about half of the transgenic grains were detected. An immunoreactive band was observed in the endosperm extracts (tracks 1, 2, 9 and 10).

Estimation of the Quantity of Lysine-Enriched γ-zeins in the Endosperms of 45γZ Transformants αG2 is a polyclonal antiserum which recognises endogenous γ-zeins and lysine-enriched γ-zeins. The reactivity of this antiserum with extracts of 45γZ C1 endosperms was used to quantify the quantity of lysine-enriched γ-zeins of the invention in the endosperms of transformed plants.

FIG. 15B shows the immunoblot of 5 protein extracts corresponding to 5 45γZ C1 endosperms (tracks 1 to 5). As expected, only 2 endosperms showed an immunoreaction profile characteristic of transgenic grains. The upper band of 30 kDa corresponded to lysine-enriched γ-zein (arrows on track 1 and 2) and the lower band corresponded to endogenous γ-zein. It should be noted that in the endosperms of non transgenic plants, the upper band was absent (tracks 3, 4 and 15). Surprisingly, it appears that the amount of endogenous γ-zein was lower in the transgenic plant extracts than in non transgenic plants (see arrows in tracks 1 and 5).

At first sight, it was observed that:
i) in 45γZ C1 transgenic endosperms, the ratio of lysine-enriched γ-zein/endogenic γ-zein was 7/3. Thus the quantity of modified protein of the invention was at least twice that of the endogenous protein;
ii) the quantity of endogenic protein in the non transgenic endosperms (see tracks 3, 4 and 5) was equivalent to that of the lysine-enriched γ-zein in the transgenic endosperms (see tracks 1 and 2).

7) Expression of Recombinant Lysine-Enriched γ-zeins in Wheat

As in Example 6), it is possible to demonstrate the presence of lysine-enriched γ-zeins of the invention in wheat.

Wheat can be transformed using the method described by Weeks et al., 1993, Plant Physiol., vol 102: pages 1077-1084 or using the method described in EP-A-0 709 462.

The invention claimed is:

1. An oligonucleotide consisting of:
   (a) one concatenation coding for a polypeptide with formula $(P-K)_n$, where:

n is selected from the group consisting of 3 (SEQ ID NO:12), 4 (SEQ ID NO:13), 5 (SEQ ID NO:14), 6 (SEQ ID NO:15), 7 (SEQ ID NO:16), 8 (SEQ ID NO:17), 9 (SEQ ID NO:18), 10 (SEQ ID NO:19), and 15 (SEQ ID NO:20);

P represents a proline amino acid residue;

K represents a lysine amino acid residue;

the symbol "—" represents a bond between the two amino acid residues, the n (P—K) units also being bonded together by such bonds; and (b) optionally at least one lysine residue at the 5' end or the 3' end of said concatenation, or both.

2. An oligonucleotide consisting of:
   (a) one concatenation coding for a polypeptide with formula $(P-K)_n$, where n is selected from the group consisting of 4 (SEQ ID NO:13), 6 (SEQ ID NO:15), 7 (SEQ ID NO:16), 8 (SEQ ID NO:17), 9 (SEQ ID NO:18), 10 (SEQ ID NO:19), and 15 (SEQ ID NO:20), where P represents a proline amino acid residue, K represents a lysine amino acid residue, and the symbol "—" represents a bond between the two amino acids residues, the n (P—K) units also being bonded together by such bonds; and (b) one or more codons at the 5' or 3' end of said concatenation, wherein the polypeptide coded for by said oligonucleotide, when incorporated into a γ-zein protein at an allowable site, allows for expression of the modified γ-zein protein in a plant cell and allows for similar or identical localization of said modified γ-zein protein as compared to the unmodified protein in a plant cell.

3. The oligonucleotide of claim 2, wherein said one or more codons comprise at least one lysine residue, wherein said at least one lysine residue is at the 5' end or the 3' end of said concatenation, or both.

4. An oligonucleotide consisting of:
(a) a concatenation coding for a polypeptide with formula (P—K)$_n$, where:
n is selected from the group consisting of 4 (SEQ ID NO:13), 5 (SEQ ID NO:14), 6 (SEQ ID NO:15), 7 (SEQ ID NO:16), 8 (SEQ ID NO:17), 9 (SEQ ID NO:18), 10 (SEQ ID NO:19), and 15 (SEQ ID NO:20);
P represents a proline amino acid residue;
K represents a lysine amino acid residue;
The symbol "—" represents a bond between the two amino acid residues, the n (P—K) units also being bonded together by such bonds, wherein said concatenation is interrupted once between two (P—K) units by amino acids that are neither P nor K; and
(b) optionally at least one lysine residue at the 5' end or the 3' end of said concatenation, wherein the polypeptide coded for by said oligonucleotide, when incorporated into a γ-zein protein at an allowable site, allows for expression of the modified γ-zein protein in a plant cell and allows for similar or identical localization of said modified γ-zein protein as compared to the unmodified protein in a plant cell.

5. An oligonucleotide consisting of:
(a) one concatenation coding for a polypeptide with formula (P—K)$_n$, where n is selected from the group consisting of 7 (SEQ ID NO:16), 8 (SEQ ID NO:17), 9 (SEQ ID NO:18), 10 (SEQ ID NO:19), and 15 (SEQ ID NO:20), where P represents a proline amino acid residue, K represents a lysine amino acid residue, the symbol "—" represents a bond between the two amino acid residues, the n (P—K) units also being bonded together by such bonds, wherein said concatenation is interrupted once between two (P—K) units by amino acids that are neither P nor K; and
(b) one or more codons at the 5' end or the 3' end of said concatenation, wherein the polypeptide coded for by said oligonucleotide, when incorporated into a γ-zein protein at an allowable site, allows for expression of the modified γ-zein protein in a plant cell and allows for similar or identical localization of said modified γ-zein protein as compared to the unmodified protein in a plant cell.

6. The oligonucleotide of claim 1, 2, 4, or 5, wherein said bonds are peptide bonds.

7. The oligonucleotide of claim 4, wherein said interruption comprises at least one lysine codon at the 3' end of said interruption.

8. An oligonucleotide having the formula K—(P—K)$_4$ (SEQ ID NO:21), 2K(P—K)$_4$ (SEQ ID NO:23), or K—(P—K)$_4$ E—F—K—(P—K)$_4$ (SEQ ID NO: 24).

9. A recombinant nucleotide sequence comprising a nucleic acid coding for a maize γ-zein of 28 kDa, wherein said recombinant nucleotide sequence further comprises an oligonucleotide:
(a) one concatenation coding for a polypeptide with formula (P—K)$_n$, where n is selected from the group consisting of 2 (SEQ ID NO:25), 3 (SEQ ID NO:12), 4 (SEQ ID NO:13), 5 (SEQ ID NO:14), 6 (SEQ ID NO:15), 7 (SEQ ID NO:16), 8 (SEQ ID NO:17), 9 (SEQ ID NO:18), 10 (SEQ ID NO:19), and 15 (SEQ ID NO:20), or
(b) one concatenation coding for a polypeptide with formula (P—K)$_n$, where n is selected from the group consisting of 2 (SEQ ID NO:25), 3 (SEQ ID NO:12), 4 (SEQ ID NO:13), 5 (SEQ ID NO:14), 6 (SEQ ID NO:15), 7 (SEQ ID NO:16), 8 (SEQ ID NO:17), 9 (SEQ ID NO:18), 10 (SEQ ID NO:19), and 15 (SEQ ID NO:20), said concatenation being interrupted once between two (P—K) units by amino acids that are neither P nor K;
where P and K represent respectively a proline and a lysine amino acid residue, the symbol "—" represents a bond between the two amino acids residues, the n (P—K) units also being bonded together by such bonds; said concatenation being inserted at one site of the nucleic acid selected such that:
i) expression of the recombinant nucleotide sequence in a particular plant cell enables the modified γ-zein to be produced, wherein said modified γ-zein is localized in that cell in a manner identical to or similar to the normal protein reserve which would be expressed in the same cell under the same conditions by the corresponding normal nucleic acid, or
ii) the modified γ-zein coded by the recombinant nucleotide sequence is immunologically recognized by antibodies produced against the corresponding normal γ-zein.

10. The recombinant nucleotide sequence of claim 9, wherein the nucleic acid coding for the maize γ-zein has the sequence set forth in SEQ ID NO:6.

11. The recombinant nucleotide sequence of claim 9, wherein the oligonucleotide is inserted in place of or following a Pro-X domain or in a Pro-X domain naturally present in the maize γ-zein.

12. The recombinant nucleotide sequence of claim 9, wherein the sequence is under the control of an expression promoter.

13. The recombinant nucleotide sequence of claim 12, wherein the promoter is a specific promoter for a given cell tissue or a promoter specific for expression in grains or in the leaves of plants.

14. The recombinant nucleotide sequence of claim 12, wherein the expression promoter is that of maize γ-zein.

15. The recombinant nucleotide sequence of claim 12, wherein the expression promoter is the promoter CaMV35S.

16. The recombinant nucleotide sequence of claim 11, which codes for one of the polypeptides P20γZ or H45γZ having the sequence set forth in SEQ ID NO:9 or SEQ ID NO:11, respectively.

17. The recombinant nucleotide sequence of claim 9, wherein the oligonucleotide is inserted following or in place of a primary structure having tandem repeats rich in proline residues.

18. A cloning or expression vector comprising, at a site which is not essential for replication, the recombinant nucleotide sequence of claim 9.

19. A recombinant host cell comprising the recombinant nucleotide sequence of claim 9.

20. The host cell of claim 19, wherein said cell is a bacterium.

21. The host cell of claim 20, wherein said bacterium is *Escherichia coli* or *Agrobacterium tumefaciens*.

22. The host cell of claim 19, which is a plant cell.

23. The host cell of claim 22, wherein said plant cell is a plant seed cell.

24. The host cell of claim 23, wherein said plant seed cell is a cell from maize seed endosperm.

25. The host cell of claim 24, wherein the recombinant nucleotide sequence is stably integrated in the genome of the host cell.

26. The host cell of claim 24, which produces a lysine-enriched modified maize γ-zein upon expression of the recombinant nucleotide sequence.

27. A maize plant producing a polypeptide encoded by the recombinant nucleotide sequence of claim 9.

28. A method for producing a maize plant or maize seeds expressing a modified γ-zein protein reserve, which comprises the steps of:
a) transforming a plant cell with the recombinant nucleotide sequence of claim 9, or the vector of claim 18, under conditions enabling the γ-zein modified protein reserve coded by the nucleotide sequence to be expressed in a stable and functional manner;
b) regenerating plants from the plant cell transformed in step a), to obtain plants expressing the modified γ-zein protein reserve; and
c) optionally obtaining seeds from the modified plants obtained in step b).

29. Maize seeds comprising a γ-zein encoded by a recombinant nucleotide sequence comprising a nucleic acid coding for the γ-zein and, inserted at one site of the nucleic acid, an oligonucleotide consisting of one concatenation coding for a polypeptide with formula $(P—K)_n$, where:
(a) n is selected from the group consisting of 2 (SEQ ID NO:25), 3 (SEQ ID NO:12), 4 (SEQ ID NO:13), 5 (SEQ ID NO:14), 6 (SEQ ID NO:15), 7 (SEQ ID NO:16), 8 (SEQ ID NO:17), 9 (SEQ ID NO:18), 10 (SEQ ID NO:19), and 15 (SEQ ID NO:20) or;
(b) n is selected from the group consisting of 2 (SEQ ID NO:25), 3 (SEQ ID NO:12), 4 (SEQ ID NO:13), 5 (SEQ ID NO:14), 6 (SEQ ID NO:15), 7 (SEQ ID NO:16), 8 (SEQ ID NO:17), 9 (SEQ ID NO:18), 10 (SEQ ID NO:19), and 15 (SEQ ID NO:20), said concatenation being interrupted once between two (P—K) units by amino acids that are neither P nor K;
where P represents a proline amino acid residue, K represents a lysine amino acid residue, and the symbol "—" represents a bond between the two amino acid residues, the n (P—K) units also being bonded together by such bonds;
wherein the insertion site of the oligonucleotide is selected such that:
i) expression of the recombinant nucleotide sequence in a particular plant cell enables a modified γ-zein protein reserve to be produced, wherein said γ-zein protein reserve is localized in that cell in a manner identical to or similar to the normal γ-zein protein reserve which would be expressed in the same cell under the same conditions by the corresponding normal nucleic acid; or
ii) the modified γ-zein protein reserve coded by the recombinant nucleotide sequence is immunologically recognized by antibodies produced against the corresponding normal γ-zein.

30. The maize seeds of claim 29, wherein said γ-zein is a maize γ-zein of 28 kDa.

31. The maize seeds of claim 29, wherein said bonds are peptide-type bonds.

32. The maize seeds of claim 29, wherein the oligonucleotide further codes for at least one lysine residue at the 5' or 3' end and the polypeptide coded for by the oligonucleotide is present within the N-terminal domain of the maize γ-zein.

33. The maize seeds of claim 32, wherein the oligonucleotide comprising at least one concatenation codes for a polypeptide having the formula $K—(P—K)_4$ (SEQ ID NO:21) or $2K(P—K)_4$ (SEQ ID NO:23).

34. The maize seeds of claim 29, wherein the plant protein is the maize γ-zein having the sequence set forth in SEQ ID NO:6.

35. The maize seeds of claim 34, wherein the oligonucleotide is inserted in place of or following a Pro-X domain or in a Pro-X domain naturally present in the maize γ-zein.

36. The maize seeds of claim 35, wherein the nucleotide sequence codes for one of the polypeptides P20γZ or H45γZ having the sequence set forth in SEQ ID NO:9 or SEQ ID NO:11, respectively.

37. A cloning and/or expression vector, which is one of plasmids pP20γZ (CNCM No I-1640), pH30γZ or pH45γZ (CNCM No I-1639).

38. The maize seeds of claim 29, wherein the oligonucleotide codes for a polypeptide having the formula $K—(P—K)_4—E—F—(P—K)_4$ (SEQ ID NO:24).

39. A recombinant nucleotide sequence comprising a nucleic acid coding for a maize γ-zein of 28 kDa, wherein said recombinant nucleotide sequence further comprises an oligonucleotide consisting of:
(a) one concatenation coding for a polypeptide with formula $(P—K)_n$, where n is selected from the group consisting of 2 (SEQ ID NO:25), 3 (SEQ ID NO:12), 4 (SEQ ID NO:13), 5 (SEQ ID NO:14), 6 (SEQ ID NO:15), 7 (SEQ ID NO:16), 8 (SEQ ID NO:17), 9 (SEQ ID NO:18), 10 (SEQ ID NO:19), and 15 (SEQ ID NO:20) and one or more codons at the 5' or 3' end of said concatenation, or
(b) one concatenation coding for a polypeptide with formula $(P—K)_n$, where n is selected from the group consisting of 2 (SEQ ID NO:25), 3 (SEQ ID NO:12), 4 (SEQ ID NO:13), 5 (SEQ ID NO:14), 6 (SEQ ID NO:15), 7 (SEQ ID NO:16), 8 (SEQ ID NO:17), 9 (SEQ ID NO:18), 10 (SEQ ID NO:19), and 15 (SEQ ID NO:20), and one or more codons at the 5' or 3' end of said concatenation, wherein said concatenation is interrupted once between two (P—K) units by amino acids that are neither P nor K;
where P and K represent respectively a proline and a lysine amino acid residue, the symbol "—" represents a bond between the two amino acids residues, the n (P—K) units also being bonded together by such bonds; and wherein said oligonucleotide is inserted at one site of the nucleic acid selected such that:
i) expression of the recombinant nucleotide sequence in a particular plant cell enables the modified γ-zein to be produced, wherein said modified γ-zein is localized in that cell in a manner identical to or similar to the normal protein reserve which would be expressed in the same cell under the same conditions by the corresponding normal nucleic acid; or ii) the modified γ-zein coded by the recombinant nucleotide sequence is immunologically recognized by antibodies produced against the corresponding normal γ-zein.

40. The recombinant nucleotide of claim 39, wherein said one or more codons comprise at least one lysine residue at the 5' end or the 3' end of said concatenation.

41. The recombinant nucleotide of claim 9, wherein said interruption comprises at least one lysine codon at the 3' end of said interruption.

42. A plant producing the polypeptide encoded by the recombinant nucleotide sequence of claim 9 or 39.

43. A method for producing plants or seeds expressing a modified γ-zein protein reserve comprising the steps of:
  (a) transforming a plant cell with the recombinant nucleotide sequence of claim 9, or the vector of claim 18, under conditions enabling the modified γ-zein encoded by the recombinant nucleotide sequence to be expressed in a stable and functional manner;
  (b) regenerating plants from the plant cell transformed in step a), to obtain plants expressing the modified γ-zein; and
  (c) optionally obtaining seeds from the modified plants in step (b).

44. Seeds comprising a γ-zein encoded by a recombinant nucleotide sequence comprising a nucleic acid coding for the γ-zein and, inserted at on site of the nucleic acid, an oligonucleotide formed by one concatenation coding for a polypeptide with formula $(P-K)_n$, where:
  n is selected from the group consisting of 2 (SEQ ID NO:25), 3 (SEQ ID NO:12), 4 (SEQ ID NO:13), 5 (SEQ ID NO:14), 6 (SEQ ID NO:15), 7 (SEQ ID NO: 16), 8 (SEQ ID NO:17), 9 (SEQ ID NO:18), 10 (SEQ ID NO: 19) and 15 (SEQ ID NO:20);
  P represents a proline amino acid residue;
  K represents a lysine amino acid residue; and
  the symbol "—" represents a bond between the two amino acid residues, the n (P—K) units also being bonded together by such bonds;
wherein the insertion site of the oligonucleotide is selected such that:
  i) expression of the recombinant nucleotide sequence in a particular plant cell enables a modified γ-zein to be produced, wherein said modified γ-zein is localized in that cell in a manner identical to or similar to the normal γ-zein which would be expressed in the same cell under the same conditions by the corresponding normal nucleic acid; or
  ii) the modified γ-zein encoded by the recombinant nucleotide sequence is immunologically recognized by antibodies produced against the corresponding normal gamma zein.

* * * * *

SEQUENCE LISTING

```
<160> NUMBER OF SEQ ID NOS: 25

<210> SEQ ID NO 1
<211> LENGTH: 44
<212> TYPE: DNA
<213> ORGANISM: Artificial Sequence
```

-continued

```
<220> FEATURE:
<223> OTHER INFORMATION: based on Maize

<400> SEQUENCE: 1
cgatgaattc aaaccaaagc caaagccgaa gccaaaagaa ttca                    44

<210> SEQ ID NO 2
<211> LENGTH: 46
<212> TYPE: DNA
<213> ORGANISM: Artificial Sequence
<220> FEATURE:
<223> OTHER INFORMATION: based on Maize

<400> SEQUENCE: 2
agcttgaatt cttttggctt cggctttggc tttggtttga attcat                  46

<210> SEQ ID NO 3
<211> LENGTH: 17
<212> TYPE: PRT
<213> ORGANISM: Maize

<400> SEQUENCE: 3

Ile Glu Phe Lys Pro Lys Pro Lys Pro Lys Pro Lys Glu Phe Leu Gln
1               5                   10                  15

Pro

<210> SEQ ID NO 4
<211> LENGTH: 28
<212> TYPE: PRT
<213> ORGANISM: Maize

<400> SEQUENCE: 4

Ile Glu Phe Lys Pro Lys Pro Lys Pro Lys Pro Lys Glu Phe Lys Pro
1               5                   10                  15
Lys Pro Lys Pro Lys Pro Lys Glu Phe Leu Gln Pro
            20                  25

<210> SEQ ID NO 5
<211> LENGTH: 20
<212> TYPE: PRT
<213> ORGANISM: Maize

<400> SEQUENCE: 5

Asp Gly Ile Asp Glu Phe Lys Pro Lys Pro Lys Pro Lys Pro Lys Glu
1               5                   10                  15
Phe Lys Leu Asp
            20

<210> SEQ ID NO 6
<211> LENGTH: 672
<212> TYPE: DNA
<213> ORGANISM: Maize
<220> FEATURE:
<221> NAME/KEY: CDS
<222> LOCATION: (1)..(672)

<400> SEQUENCE: 6 atg agg gtg ttg ctc gtt gcc ctc gct ctc ctg gct ctc gct gcg agc    48
Met Arg Val Leu Leu Val Ala Leu Ala Leu Leu Ala Leu Ala Ala Ser
1               5                   10                  15 gcc acc tcc acg cat aca agc ggc ggc tgc ggc tgc cag cca ccg ccg    96
Ala Thr Ser Thr His Thr Ser Gly Gly Cys Gly Cys Gln Pro Pro Pro
            20                  25                  30
```

```
ccg gtt cat cta ccg ccg gtg cat ctg cca cct ccg gtt cac ctg         144
Pro Val His Leu Pro Pro Val His Leu Pro Pro Pro Val His Leu
             35                  40                  45 cca cct ccg gtg cat ctc cca ccg ccg gtc cac ctg ccg ccg gtc         192
Pro Pro Pro Val His Leu Pro Pro Pro Val His Leu Pro Pro Val
 50                  55                  60 cac ctg cca ccg ccg gtc cat gtg ccg ccg gtt cat ctg ccg ccg         240
His Leu Pro Pro Pro Val His Val Pro Pro Val His Leu Pro Pro
 65                  70                  75                  80 cca cca tgc cac tac cct act caa ccg ccc cgg cct cag cct cat ccc     288
Pro Pro Cys His Tyr Pro Thr Gln Pro Pro Arg Pro Gln Pro His Pro
             85                  90                  95 cag cca cac cca tgc ccg tgc caa cag ccg cat cca agc ccg tgc cag     336
Gln Pro His Pro Cys Pro Cys Gln Gln Pro His Pro Ser Pro Cys Gln
                 100                 105                 110 ctg cag gga acc tgc ggc gtt ggc agc acc ccg atc ctg ggc cag tgc     384
Leu Gln Gly Thr Cys Gly Val Gly Ser Thr Pro Ile Leu Gly Gln Cys
             115                 120                 125 gtc gag ttt ctg agg cat cag tgc agc ccg acg gcg acg ccc tac tgc     432
Val Glu Phe Leu Arg His Gln Cys Ser Pro Thr Ala Thr Pro Tyr Cys
         130                 135                 140 tcg cct cag tgc cag tcg ttg cgg cag cag tgt tgc cag cag ctc agg     480
Ser Pro Gln Cys Gln Ser Leu Arg Gln Gln Cys Cys Gln Gln Leu Arg
145                 150                 155                 160 cag gtg gag ccg cag cac cgg tac cag gcg atc ttc ggc ttg gtc ctc     528
Gln Val Glu Pro Gln His Arg Tyr Gln Ala Ile Phe Gly Leu Val Leu
                 165                 170                 175 cag tcc atc ctg cag cag cag ccg caa agc ggc cag gtc gcg ggg ctg     576
Gln Ser Ile Leu Gln Gln Gln Pro Gln Ser Gly Gln Val Ala Gly Leu
             180                 185                 190 ttg gcg gcg cag ata gcg cag caa ctg acg gcg atg tgc ggc ctg cag     624
Leu Ala Ala Gln Ile Ala Gln Gln Leu Thr Ala Met Cys Gly Leu Gln
         195                 200                 205 cag ccg act cca tgc ccc tac gct gct gcc ggc ggt gtc ccc cac tga     672
Gln Pro Thr Pro Cys Pro Tyr Ala Ala Ala Gly Gly Val Pro His
210                 215                 220
```

<210> SEQ ID NO 7
<211> LENGTH: 223
<212> TYPE: PRT
<213> ORGANISM: Maize

<400> SEQUENCE: 7

```
Met Arg Val Leu Leu Val Ala Leu Ala Leu Leu Ala Leu Ala Ala Ser
 1               5                  10                  15

Ala Thr Ser Thr His Thr Ser Gly Gly Cys Gly Cys Gln Pro Pro Pro
             20                  25                  30

Pro Val His Leu Pro Pro Pro Val His Leu Pro Pro Pro Val His Leu
             35                  40                  45

Pro Pro Pro Val His Leu Pro Pro Pro Val His Leu Pro Pro Pro Val
 50                  55                  60

His Leu Pro Pro Pro Val His Val Pro Pro Val His Leu Pro Pro
 65                  70                  75                  80

Pro Pro Cys His Tyr Pro Thr Gln Pro Pro Arg Pro Gln Pro His Pro
             85                  90                  95

Gln Pro His Pro Cys Pro Cys Gln Gln Pro His Pro Ser Pro Cys Gln
                 100                 105                 110

Leu Gln Gly Thr Cys Gly Val Gly Ser Thr Pro Ile Leu Gly Gln Cys
             115                 120                 125
```

```
Val Glu Phe Leu Arg His Gln Cys Ser Pro Thr Ala Thr Pro Tyr Cys
    130                 135                 140

Ser Pro Gln Cys Gln Ser Leu Arg Gln Gln Cys Cys Gln Gln Leu Arg
145                 150                 155                 160

Gln Val Glu Pro Gln His Arg Tyr Gln Ala Ile Phe Gly Leu Val Leu
                165                 170                 175

Gln Ser Ile Leu Gln Gln Pro Gln Ser Gly Gln Val Ala Gly Leu
            180                 185                 190

Leu Ala Ala Gln Ile Ala Gln Gln Leu Thr Ala Met Cys Gly Leu Gln
            195                 200                 205

Gln Pro Thr Pro Cys Pro Tyr Ala Ala Ala Gly Gly Val Pro His
    210                 215                 220

<210> SEQ ID NO 8
<211> LENGTH: 693
<212> TYPE: DNA
<213> ORGANISM: maize
<220> FEATURE:
<221> NAME/KEY: CDS
<222> LOCATION: (1)..(693)

<400> SEQUENCE: 8 atg agg gtg ttg ctc gtt gcc ctc gct ctc ctg gct ctc gct gcg agc      48
Met Arg Val Leu Leu Val Ala Leu Ala Leu Leu Ala Leu Ala Ala Ser
1               5                   10                  15 gcc acc tcc acg cat aca agc ggc ggc tgc ggc tgc cag cca ccg ccg      96
Ala Thr Ser Thr His Thr Ser Gly Gly Cys Gly Cys Gln Pro Pro Pro
                20                  25                  30 ccg gtt cat cta ccg ccg ccg gtg cat ctg cca cct ccg gtt cac ctg     144
Pro Val His Leu Pro Pro Pro Val His Leu Pro Pro Pro Val His Leu
            35                  40                  45 cca cct ccg gtg cat ctc cca ccg ccg gtc cac ctg ccg ccg ccg gtc     192
Pro Pro Pro Val His Leu Pro Pro Pro Val His Leu Pro Pro Pro Val
        50                  55                  60 cac ctg cca ccg ccg gtc cat gtg ccg ccg ccg gtt cat ctg ccg ccg     240
His Leu Pro Pro Pro Val His Val Pro Pro Pro Val His Leu Pro Pro
65                  70                  75                  80 cca cca tgc cac tac cct act caa ccg ccc cgg atc gaa ttc aaa cca     288
Pro Pro Cys His Tyr Pro Thr Gln Pro Pro Arg Ile Glu Phe Lys Pro
                85                  90                  95 aag cca aag ccg aag cca aaa gaa ttc aaa cca aag cca aag ccg aag     336
Lys Pro Lys Pro Lys Pro Lys Glu Phe Lys Pro Lys Pro Lys Pro Lys
                100                 105                 110 cca aaa gaa ttc ctg cag ccc ctg cag gga acc tgc ggc gtt ggc agc     384
Pro Lys Glu Phe Leu Gln Pro Leu Gln Gly Thr Cys Gly Val Gly Ser
            115                 120                 125 acc ccg atc ctg ggc cag tgc gtc gag ttt ctg agg cat cag tgc agc     432
Thr Pro Ile Leu Gly Gln Cys Val Glu Phe Leu Arg His Gln Cys Ser
        130                 135                 140 ccg acg gcg acg ccc tac tgc tcg cct cag tgc cag tcg ttg cgg cag     480
Pro Thr Ala Thr Pro Tyr Cys Ser Pro Gln Cys Gln Ser Leu Arg Gln
145                 150                 155                 160 cag tgt tgc cag cag ctc agg cag gtg gag ccg cag cac cgg tac cag     528
Gln Cys Cys Gln Gln Leu Arg Gln Val Glu Pro Gln His Arg Tyr Gln
                165                 170                 175 gcg atc ttc ggc ttg gtc ctc cag tcc atc ctg cag cag ccg caa         576
Ala Ile Phe Gly Leu Val Leu Gln Ser Ile Leu Gln Gln Pro Gln
            180                 185                 190 agc ggc cag gtc gcg ggg ctg ttg gcg gcg cag ata gcg cag caa ctg     624
Ser Gly Gln Val Ala Gly Leu Leu Ala Ala Gln Ile Ala Gln Gln Leu
```

```
                                                                             -continued Ser Gly Gln Val Ala Gly Leu Leu Ala Ala Gln Ile Ala Gln Gln Leu
        195                 200                 205 acg gcg atg tgc ggc ctg cag cag ccg act cca tgc ccc tac gct gct              672
Thr Ala Met Cys Gly Leu Gln Gln Pro Thr Pro Cys Pro Tyr Ala Ala
    210                 215                 220 gcc ggc ggt gtc ccc cac tga                                                  693
Ala Gly Gly Val Pro His
225                 230

<210> SEQ ID NO 9
<211> LENGTH: 230
<212> TYPE: PRT
<213> ORGANISM: maize

<400> SEQUENCE: 9

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Pro Val His Leu
        35                  40                  45

Pro Pro Pro Val His Leu Pro Pro Pro Val His Leu Pro Pro Pro Val
    50                  55                  60

His Leu Pro Pro Pro Val His Val Pro Pro Pro Val His Leu Pro Pro
65                  70                  75                  80

Pro Pro Cys His Tyr Pro Thr Gln Pro Pro Arg Ile Glu Phe Lys Pro
                85                  90                  95

Lys Pro Lys Pro Lys Pro Lys Glu Phe Lys Pro Lys Pro Lys Pro Lys
            100                 105                 110

Pro Lys Glu Phe Leu Gln Pro Leu Gln Gly Thr Cys Gly Val Gly Ser
        115                 120                 125

Thr Pro Ile Leu Gly Gln Cys Val Glu Phe Leu Arg His Gln Cys Ser
    130                 135                 140

Pro Thr Ala Thr Pro Tyr Cys Ser Pro Gln Cys Gln Ser Leu Arg Gln
145                 150                 155                 160

Gln Cys Cys Gln Gln Leu Arg Gln Val Glu Pro Gln His Arg Tyr Gln
                165                 170                 175

Ala Ile Phe Gly Leu Val Leu Gln Ser Ile Leu Gln Gln Gln Pro Gln
            180                 185                 190

Ser Gly Gln Val Ala Gly Leu Leu Ala Ala Gln Ile Ala Gln Gln Leu
        195                 200                 205

Thr Ala Met Cys Gly Leu Gln Gln Pro Thr Pro Cys Pro Tyr Ala Ala
    210                 215                 220

Ala Gly Gly Val Pro His
225                 230

<210> SEQ ID NO 10
<211> LENGTH: 723
<212> TYPE: DNA
<213> ORGANISM: Maize
<220> FEATURE:
<221> NAME/KEY: CDS
<222> LOCATION: (1)..(723)

<400> SEQUENCE: 10 atg agg gtg ttg ctc gtt gcc ctc gct ctc ctg gct ctc gct gcg agc              48
Met Arg Val Leu Leu Val Ala Leu Ala Leu Leu Ala Leu Ala Ala Ser
1               5                   10                  15
```

-continued

```
gcc acc tcc acg cat aca agc ggc ggc tgc ggc tgc cag cca ccg ccg      96
Ala Thr Ser Thr His Thr Ser Gly Gly Cys Gly Cys Gln Pro Pro Pro
            20                  25                  30 ccg gtt cat cta ccg ccg gtg cat ctg cca cct ccg gtt cac ctg         144
Pro Val His Leu Pro Pro Val His Leu Pro Pro Pro Val His Leu
        35                  40                  45 cca cct ccg gtg cat ctc cca ccg gtc cac ctg ccg ccg gtc             192
Pro Pro Pro Val His Leu Pro Pro Val His Leu Pro Pro Val
50                  55                  60 cac ctg cca ccg ccg gtc cat gtg ccg ccg gtt cat ctg ccg ccg         240
His Leu Pro Pro Pro Val His Val Pro Pro Val His Leu Pro Pro
65                  70                  75                  80 cca cca tgc cac tac cct act caa ccg ccc cgg cct cag cct cat ccc     288
Pro Pro Cys His Tyr Pro Thr Gln Pro Pro Arg Pro Gln Pro His Pro
                85                  90                  95 cag cca cac cca tgc ccg tgc caa cag ccg cat cca agc ccg tgc cag     336
Gln Pro His Pro Cys Pro Cys Gln Gln Pro His Pro Ser Pro Cys Gln
            100                 105                 110 atc gaa ttc aaa cca aag cca aag ccg aag cca aaa gaa ttc ctg cag     384
Ile Glu Phe Lys Pro Lys Pro Lys Pro Lys Pro Lys Glu Phe Leu Gln
        115                 120                 125 ccc ctg cag gga acc tgc ggc gtt ggc agc acc ccg atc ctg ggc cag     432
Pro Leu Gln Gly Thr Cys Gly Val Gly Ser Thr Pro Ile Leu Gly Gln
130                 135                 140 tgc gtc gag ttt ctg agg cat cag tgc agc ccg acg gcg acg ccc tac     480
Cys Val Glu Phe Leu Arg His Gln Cys Ser Pro Thr Ala Thr Pro Tyr
145                 150                 155                 160 tgc tcg cct cag tgc cag tcg ttg cgg cag cag tgt tgc cag cag ctc     528
Cys Ser Pro Gln Cys Gln Ser Leu Arg Gln Gln Cys Cys Gln Gln Leu
                165                 170                 175 agg cag gtg gag ccg cag cac cgg tac cag gcg atc ttc ggc ttg gtc     576
Arg Gln Val Glu Pro Gln His Arg Tyr Gln Ala Ile Phe Gly Leu Val
            180                 185                 190 ctc cag tcc atc ctg cag cag cag ccg caa agc ggc cag gtc gcg ggg     624
Leu Gln Ser Ile Leu Gln Gln Gln Pro Gln Ser Gly Gln Val Ala Gly
        195                 200                 205 ctg ttg gcg gcg cag ata gcg cag caa ctg acg gcg atg tgc ggc ctg     672
Leu Leu Ala Ala Gln Ile Ala Gln Gln Leu Thr Ala Met Cys Gly Leu
210                 215                 220 cag cag ccg act cca tgc ccc tac gct gct gcc ggc ggt gtc ccc cac     720
Gln Gln Pro Thr Pro Cys Pro Tyr Ala Ala Ala Gly Gly Val Pro His
225                 230                 235                 240 tga                                                                 723
```

<210> SEQ ID NO 11
<211> LENGTH: 240
<212> TYPE: PRT
<213> ORGANISM: Maize

<400> SEQUENCE: 11

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Val His Leu Pro Pro Val His Leu
        35                  40                  45

Pro Pro Pro Val His Leu Pro Pro Val His Leu Pro Pro Val
50                  55                  60

His Leu Pro Pro Pro Val His Val Pro Pro Val His Leu Pro Pro
```

-continued

```
                65                  70                  75                  80
            Pro Pro Cys His Tyr Pro Thr Gln Pro Pro Arg Pro Gln Pro His Pro
                            85                  90                  95

Gln Pro His Pro Cys Pro Cys Gln Gln Pro His Pro Ser Pro Cys Gln
                        100                 105                 110

Ile Glu Phe Lys Pro Lys Pro Lys Pro Lys Glu Phe Leu Gln
                    115                 120                 125

Pro Leu Gln Gly Thr Cys Gly Val Gly Ser Thr Pro Ile Leu Gly Gln
                    130                 135                 140

Cys Val Glu Phe Leu Arg His Gln Cys Ser Pro Thr Ala Thr Pro Tyr
            145                 150                 155                 160

Cys Ser Pro Gln Cys Gln Ser Leu Arg Gln Gln Cys Cys Gln Gln Leu
                        165                 170                 175

Arg Gln Val Glu Pro Gln His Arg Tyr Gln Ala Ile Phe Gly Leu Val
                        180                 185                 190

Leu Gln Ser Ile Leu Gln Gln Pro Gln Ser Gly Gln Val Ala Gly
                    195                 200                 205

Leu Leu Ala Ala Gln Ile Ala Gln Gln Leu Thr Ala Met Cys Gly Leu
                    210                 215                 220

Gln Gln Pro Thr Pro Cys Pro Tyr Ala Ala Ala Gly Gly Val Pro His
            225                 230                 235                 240

<210> SEQ ID NO 12
<211> LENGTH: 6
<212> TYPE: PRT
<213> ORGANISM: Artificial Sequence
<220> FEATURE:
<223> OTHER INFORMATION: based on Maize

<400> SEQUENCE: 12

Pro Lys Pro Lys Pro Lys
1               5

<210> SEQ ID NO 13
<211> LENGTH: 8
<212> TYPE: PRT
<213> ORGANISM: Artificial Sequence
<220> FEATURE:
<223> OTHER INFORMATION: based on Maize

<400> SEQUENCE: 13

Pro Lys Pro Lys Pro Lys Pro Lys
1               5

<210> SEQ ID NO 14
<211> LENGTH: 10
<212> TYPE: PRT
<213> ORGANISM: Artificial Sequence
<220> FEATURE:
<223> OTHER INFORMATION: based on Maize

<400> SEQUENCE: 14

Pro Lys Pro Lys Pro Lys Pro Lys Pro Lys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: based on Maize
```

```
<400> SEQUENCE: 15

Pro Lys Pro Lys Pro Lys Pro Lys Pro Lys Pro Lys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: based on Maize

<400> SEQUENCE: 16

Pro Lys Pro Lys Pro Lys Pro Lys Pro Lys Pro Lys Pro Lys
1               5                   10

<210> SEQ ID NO 17
<211> LENGTH: 16
<212> TYPE: PRT
<213> ORGANISM: Artificial Sequence
<220> FEATURE:
<223> OTHER INFORMATION: based on Maize

<400> SEQUENCE: 17

Pro Lys Pro Lys Pro Lys Pro Lys Pro Lys Pro Lys Pro Lys Pro Lys
1               5                   10                  15

<210> SEQ ID NO 18
<211> LENGTH: 18
<212> TYPE: PRT
<213> ORGANISM: Artificial Sequence
<220> FEATURE:
<223> OTHER INFORMATION: based on Maize

<400> SEQUENCE: 18

Pro Lys Pro Lys Pro Lys Pro Lys Pro Lys Pro Lys Pro Lys Pro Lys
1               5                   10                  15

Pro Lys

<210> SEQ ID NO 19
<211> LENGTH: 20
<212> TYPE: PRT
<213> ORGANISM: Artificial Sequence
<220> FEATURE:
<223> OTHER INFORMATION: based on Maize

<400> SEQUENCE: 19

Pro Lys Pro Lys Pro Lys Pro Lys Pro Lys Pro Lys Pro Lys Pro Lys
1               5                   10                  15

Pro Lys Pro Lys
            20

<210> SEQ ID NO 20
<211> LENGTH: 30
<212> TYPE: PRT
<213> ORGANISM: Artificial Sequence
<220> FEATURE:
<223> OTHER INFORMATION: based on Maize

<400> SEQUENCE: 20

Pro Lys Pro Lys Pro Lys Pro Lys Pro Lys Pro Lys Pro Lys Pro Lys
1               5                   10                  15

Pro Lys Pro Lys Pro Lys Pro Lys Pro Lys Pro Lys Pro Lys
            20                  25                  30
```

```
<210> SEQ ID NO 21
<211> LENGTH: 9
<212> TYPE: PRT
<213> ORGANISM: Artificial Sequence
<220> FEATURE:
<223> OTHER INFORMATION: based on Maize

<400> SEQUENCE: 21

Lys Pro Lys Pro Lys Pro Lys Pro Lys
1               5

<210> SEQ ID NO 22
<211> LENGTH: 60
<212> TYPE: PRT
<213> ORGANISM: Artificial Sequence
<220> FEATURE:
<223> OTHER INFORMATION: based on Maize
<220> FEATURE:
<221> NAME/KEY: VARIANT
<222> LOCATION: (5)..(5)
<223> OTHER INFORMATION: Xaa = Pro or is absent
<220> FEATURE:
<221> NAME/KEY: VARIANT
<222> LOCATION: (6)..(6)
<223> OTHER INFORMATION: Xaa = Lys or is absent
<220> FEATURE:
<221> NAME/KEY: VARIANT
<222> LOCATION: (7)..(7)
<223> OTHER INFORMATION: Xaa = Pro or is absent
<220> FEATURE:
<221> NAME/KEY: VARIANT
<222> LOCATION: (8)..(8)
<223> OTHER INFORMATION: Xaa = Lys or is absent
<220> FEATURE:
<221> NAME/KEY: VARIANT
<222> LOCATION: (9)..(9)
<223> OTHER INFORMATION: Xaa = Pro or is absent
<220> FEATURE:
<221> NAME/KEY: VARIANT
<222> LOCATION: (10)..(10)
<223> OTHER INFORMATION: Xaa = Lys or is absent
<220> FEATURE:
<221> NAME/KEY: VARIANT
<222> LOCATION: (11)..(11)
<223> OTHER INFORMATION: Xaa = Pro or is absent
<220> FEATURE:
<221> NAME/KEY: VARIANT
<222> LOCATION: (12)..(12)
<223> OTHER INFORMATION: Xaa = Lys or is absent
<220> FEATURE:
<221> NAME/KEY: VARIANT
<222> LOCATION: (13)..(13)
<223> OTHER INFORMATION: Xaa = Pro or is absent
<220> FEATURE:
<221> NAME/KEY: VARIANT
<222> LOCATION: (14)..(14)
<223> OTHER INFORMATION: Xaa = Lys or is absent
<220> FEATURE:
<221> NAME/KEY: VARIANT
<222> LOCATION: (15)..(15)
<223> OTHER INFORMATION: Xaa = Pro or is absent
<220> FEATURE:
<221> NAME/KEY: VARIANT
<222> LOCATION: (16)..(16)
<223> OTHER INFORMATION: Xaa = Lys or is absent
<220> FEATURE:
<221> NAME/KEY: VARIANT
<222> LOCATION: (17)..(17)
<223> OTHER INFORMATION: Xaa = Pro or is absent
<220> FEATURE:
<221> NAME/KEY: VARIANT
<222> LOCATION: (18)..(18)
<223> OTHER INFORMATION: Xaa = Lys or is absent
<220> FEATURE:
<221> NAME/KEY: VARIANT
<222> LOCATION: (19)..(19)
<223> OTHER INFORMATION: Xaa = Pro or is absent
```

```
<220> FEATURE:
<221> NAME/KEY: VARIANT
<222> LOCATION: (20)..(20)
<223> OTHER INFORMATION: Xaa = Lys or is absent
<220> FEATURE:
<221> NAME/KEY: VARIANT
<222> LOCATION: (21)..(21)
<223> OTHER INFORMATION: Xaa = Pro or is absent
<220> FEATURE:
<221> NAME/KEY: VARIANT
<222> LOCATION: (22)..(22)
<223> OTHER INFORMATION: Xaa = Lys or is absent
<220> FEATURE:
<221> NAME/KEY: VARIANT
<222> LOCATION: (23)..(23)
<223> OTHER INFORMATION: Xaa = Pro or is absent
<220> FEATURE:
<221> NAME/KEY: VARIANT
<222> LOCATION: (24)..(24)
<223> OTHER INFORMATION: Xaa = Lys or is absent
<220> FEATURE:
<221> NAME/KEY: VARIANT
<222> LOCATION: (25)..(25)
<223> OTHER INFORMATION: Xaa = Pro or is absent
<220> FEATURE:
<221> NAME/KEY: VARIANT
<222> LOCATION: (26)..(26)
<223> OTHER INFORMATION: Xaa = Lys or is absent
<220> FEATURE:
<221> NAME/KEY: VARIANT
<222> LOCATION: (27)..(27)
<223> OTHER INFORMATION: Xaa = Pro or is absent
<220> FEATURE:
<221> NAME/KEY: VARIANT
<222> LOCATION: (28)..(28)
<223> OTHER INFORMATION: Xaa = Lys or is absent
<220> FEATURE:
<221> NAME/KEY: VARIANT
<222> LOCATION: (29)..(29)
<223> OTHER INFORMATION: Xaa = Pro or is absent
<220> FEATURE:
<221> NAME/KEY: VARIANT
<222> LOCATION: (30)..(30)
<223> OTHER INFORMATION: Xaa = Lys or is absent
<220> FEATURE:
<221> NAME/KEY: VARIANT
<222> LOCATION: (31)..(31)
<223> OTHER INFORMATION: Xaa = Pro or is absent
<220> FEATURE:
<221> NAME/KEY: VARIANT
<222> LOCATION: (32)..(32)
<223> OTHER INFORMATION: Xaa = Lys or is absent
<220> FEATURE:
<221> NAME/KEY: VARIANT
<222> LOCATION: (33)..(33)
<223> OTHER INFORMATION: Xaa = Pro or is absent
<220> FEATURE:
<221> NAME/KEY: VARIANT
<222> LOCATION: (34)..(34)
<223> OTHER INFORMATION: Xaa = Lys or is absent
<220> FEATURE:
<221> NAME/KEY: VARIANT
<222> LOCATION: (35)..(35)
<223> OTHER INFORMATION: Xaa = Pro or is absent
<220> FEATURE:
<221> NAME/KEY: VARIANT
<222> LOCATION: (36)..(36)
<223> OTHER INFORMATION: Xaa = Lys or is absent
<220> FEATURE:
<221> NAME/KEY: VARIANT
<222> LOCATION: (37)..(37)
<223> OTHER INFORMATION: Xaa = Pro or is absent
<220> FEATURE:
<221> NAME/KEY: VARIANT
<222> LOCATION: (38)..(38)
<223> OTHER INFORMATION: Xaa = Lys or is absent
<220> FEATURE:
<221> NAME/KEY: VARIANT
<222> LOCATION: (39)..(39)
```

-continued

```
<223> OTHER INFORMATION: Xaa = Pro or is absent
<220> FEATURE:
<221> NAME/KEY: VARIANT
<222> LOCATION: (40)..(40)
<223> OTHER INFORMATION: Xaa = Lys or is absent
<220> FEATURE:
<221> NAME/KEY: VARIANT
<222> LOCATION: (41)..(41)
<223> OTHER INFORMATION: Xaa = Pro or is absent
<220> FEATURE:
<221> NAME/KEY: VARIANT
<222> LOCATION: (42)..(42)
<223> OTHER INFORMATION: Xaa = Lys or is absent
<220> FEATURE:
<221> NAME/KEY: VARIANT
<222> LOCATION: (43)..(43)
<223> OTHER INFORMATION: Xaa = Pro or is absent
<220> FEATURE:
<221> NAME/KEY: VARIANT
<222> LOCATION: (44)..(44)
<223> OTHER INFORMATION: Xaa = Lys or is absent
<220> FEATURE:
<221> NAME/KEY: VARIANT
<222> LOCATION: (45)..(45)
<223> OTHER INFORMATION: Xaa = Pro or is absent
<220> FEATURE:
<221> NAME/KEY: VARIANT
<222> LOCATION: (46)..(46)
<223> OTHER INFORMATION: Xaa = Lys or is absent
<220> FEATURE:
<221> NAME/KEY: VARIANT
<222> LOCATION: (47)..(47)
<223> OTHER INFORMATION: Xaa = Pro or is absent
<220> FEATURE:
<221> NAME/KEY: VARIANT
<222> LOCATION: (48)..(48)
<223> OTHER INFORMATION: Xaa = Lys or is absent
<220> FEATURE:
<221> NAME/KEY: VARIANT
<222> LOCATION: (49)..(49)
<223> OTHER INFORMATION: Xaa = Pro or is absent
<220> FEATURE:
<221> NAME/KEY: VARIANT
<222> LOCATION: (50)..(50)
<223> OTHER INFORMATION: Xaa = Lys or is absent
<220> FEATURE:
<221> NAME/KEY: VARIANT
<222> LOCATION: (51)..(51)
<223> OTHER INFORMATION: Xaa = Pro or is absent
<220> FEATURE:
<221> NAME/KEY: VARIANT
<222> LOCATION: (52)..(52)
<223> OTHER INFORMATION: Xaa = Lys or is absent
<220> FEATURE:
<221> NAME/KEY: VARIANT
<222> LOCATION: (53)..(53)
<223> OTHER INFORMATION: Xaa = Pro or is absent
<220> FEATURE:
<221> NAME/KEY: VARIANT
<222> LOCATION: (54)..(54)
<223> OTHER INFORMATION: Xaa = Lys or is absent
<220> FEATURE:
<221> NAME/KEY: VARIANT
<222> LOCATION: (55)..(55)
<223> OTHER INFORMATION: Xaa = Pro or is absent
<220> FEATURE:
<221> NAME/KEY: VARIANT
<222> LOCATION: (56)..(56)
<223> OTHER INFORMATION: Xaa = Lys or is absent
<220> FEATURE:
<221> NAME/KEY: VARIANT
<222> LOCATION: (57)..(57)
<223> OTHER INFORMATION: Xaa = Pro or is absent
<220> FEATURE:
<221> NAME/KEY: VARIANT
<222> LOCATION: (58)..(58)
<223> OTHER INFORMATION: Xaa = Lys or is absent
<220> FEATURE:
<221> NAME/KEY: VARIANT
```

```
<222> LOCATION: (59)..(59)
<223> OTHER INFORMATION: Xaa = Pro or is absent
<220> FEATURE:
<221> NAME/KEY: VARIANT
<222> LOCATION: (60)..(60)
<223> OTHER INFORMATION: Xaa = Lys or is absent

<400> SEQUENCE: 22

Pro Lys Pro Lys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

<210> SEQ ID NO 23
<211> LENGTH: 18
<212> TYPE: PRT
<213> ORGANISM: Artificial Sequence
<220> FEATURE:
<223> OTHER INFORMATION: based on Maize

<400> SEQUENCE: 23

Lys Pro Lys Pro Lys Pro Lys Pro Lys Lys Pro Lys Pro Lys Pro Lys
1               5                   10                  15

Pro Lys

<210> SEQ ID NO 24
<211> LENGTH: 20
<212> TYPE: PRT
<213> ORGANISM: Artificial Sequence
<220> FEATURE:
<223> OTHER INFORMATION: based on Maize

<400> SEQUENCE: 24

Lys Pro Lys Pro Lys Pro Lys Pro Lys Glu Phe Lys Pro Lys Pro Lys
1               5                   10                  15

Pro Lys Pro Lys
        20

<210> SEQ ID NO 25
<211> LENGTH: 4
<212> TYPE: PRT
<213> ORGANISM: Artificial Sequence
<220> FEATURE:
<223> OTHER INFORMATION: based on Maize

<400> SEQUENCE: 25

Pro Lys Pro Lys
1
```